United States Patent [19]
Han et al.

[11] Patent Number: 5,891,051
[45] Date of Patent: Apr. 6, 1999

[54] ELECTRONIC URINE MONITOR

[75] Inventors: James C. Han, Lawrenceville; Morton Wexler, Conyers; Timothy J. Kelly, Atlanta, all of Ga.; Bradley J. Denny, San Marcos, Calif.; Paul J. Mulhauser, New York, N.Y.

[73] Assignee: C.R. Bard, Inc., Murray Hill, N.J.

[21] Appl. No.: 460,503

[22] Filed: Jun. 2, 1995

[51] Int. Cl.⁶ ....................................................... A61B 5/00
[52] U.S. Cl. ........................... 600/573; 600/580; 604/318
[58] Field of Search .................................... 128/760, 630; 604/329, 317, 318, 319; 600/580

[56] References Cited

U.S. PATENT DOCUMENTS

| | | |
|---|---|---|
| D. 281,278 | 11/1985 | Blankenship et al. . |
| 3,044,663 | 7/1962 | Norton et al. . |
| 4,448,207 | 5/1984 | Parrish . |
| 4,449,969 | 5/1984 | Schweizer . |
| 4,487,606 | 12/1984 | Leviton et al. . |
| 4,658,834 | 4/1987 | Blankenship et al. . |
| 4,823,805 | 4/1989 | Wojcik . |
| 4,936,837 | 6/1990 | Wexler et al. . |
| 5,218,971 | 6/1993 | Minami et al. ........................ 128/760 |
| 5,342,328 | 8/1994 | Grossman et al. ..................... 128/760 |
| 5,529,063 | 6/1996 | Hill ....................................... 128/760 |

Primary Examiner—Max Hindenburg
Assistant Examiner—Pamela L. Wingood
Attorney, Agent, or Firm—Jones & Askew, LLP

[57] ABSTRACT

A monitor is disclosed for measuring a liquid discharged from a patient's body. A housing defines a cavity having a floor. A substantially rigid wall container is removably positioned within the cavity, the container having a bottom wall portion supported on the floor of the cavity. A transducer is mounted in the floor of the cavity and engages the bottom wall portion of the container. The transducer is periodically engaged to transmit energy through the bottom wall portion and into a pool. The time duration required for the transmitted energy to travel from the transducer means to the upper surface of the pool and back again is determined, and this time duration is converted into a volume of fluid by reference to a look-up table, a mathematical algorithm, or both. The monitor includes an optical sensor to detect the presence of a container in the housing and provides an indication if no container is detected. The monitor also includes a transducer driving routine which drives the transducer at more than one output energy level, and responsive to detection of a weak return signal, the output energy level of a succeeding pulse is increased. A novel container is disclosed which includes a small well directly above the transducer, which has the effect of concentrating initial small amounts of liquid directly above the transducer to permit accurate readings of minute volumes of liquid.

7 Claims, 16 Drawing Sheets

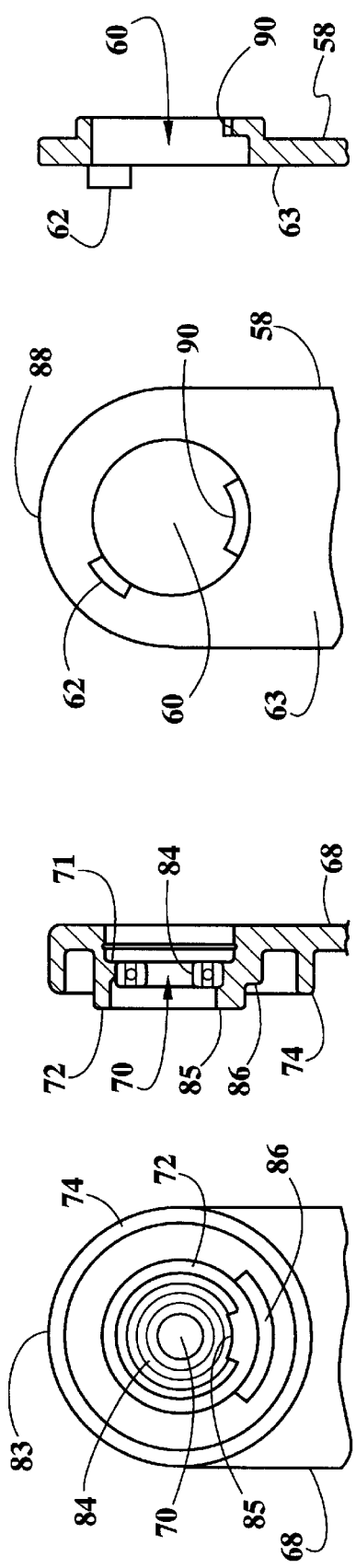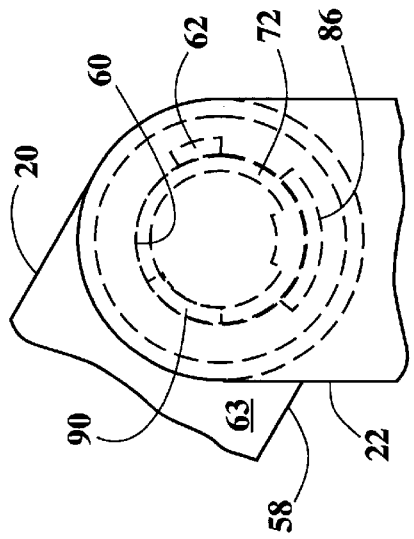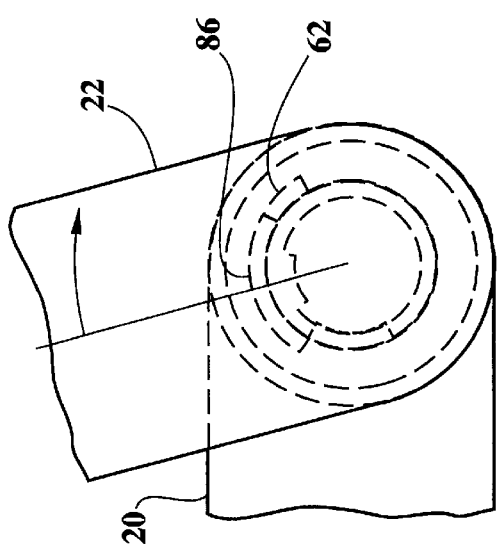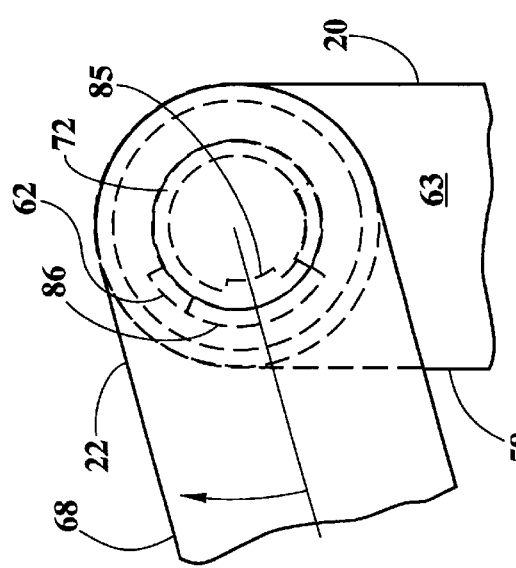

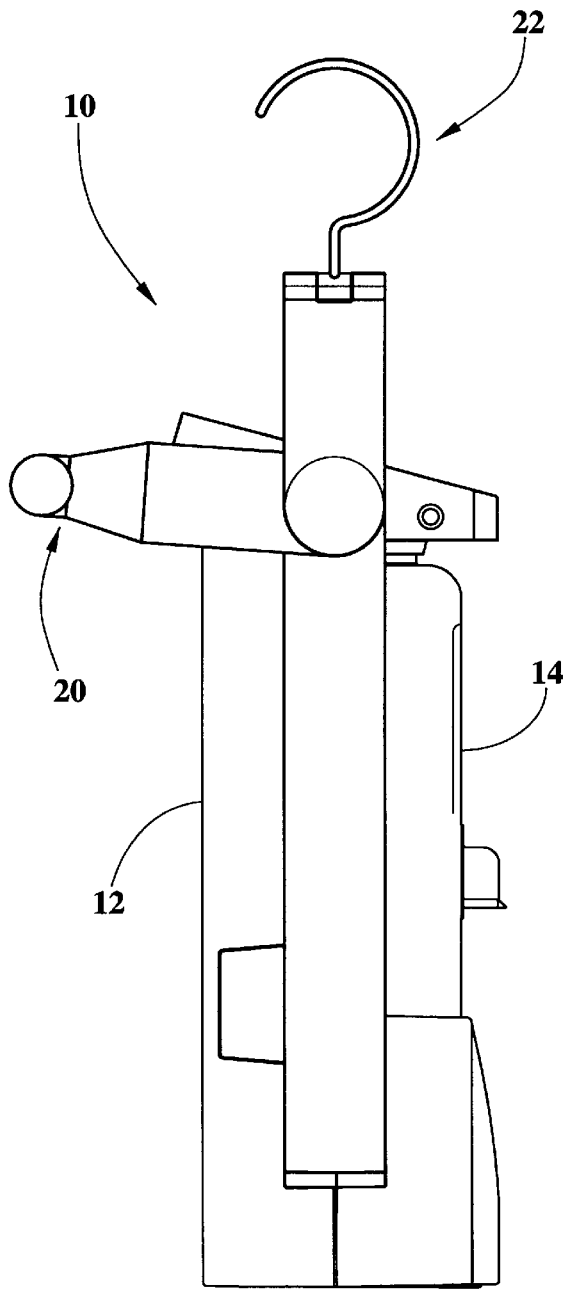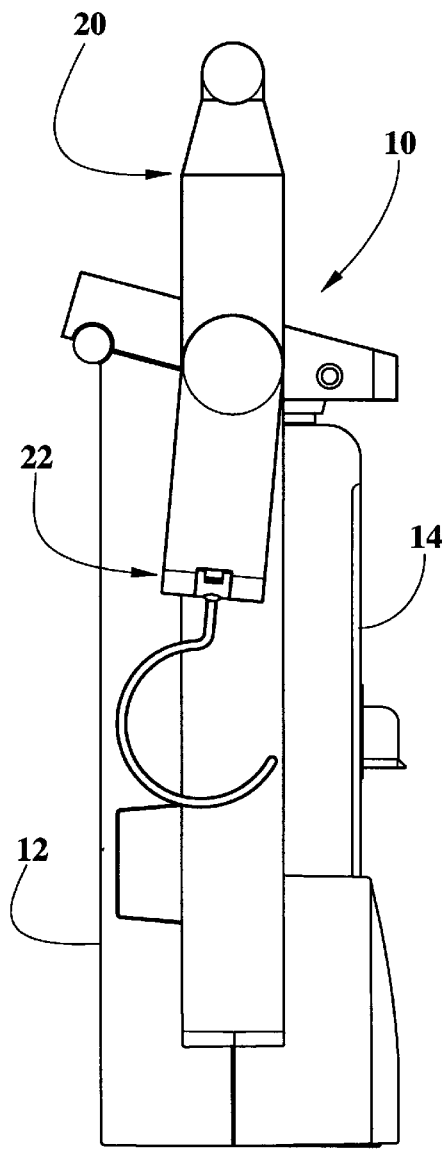
*Fig. 10*   *Fig. 11*

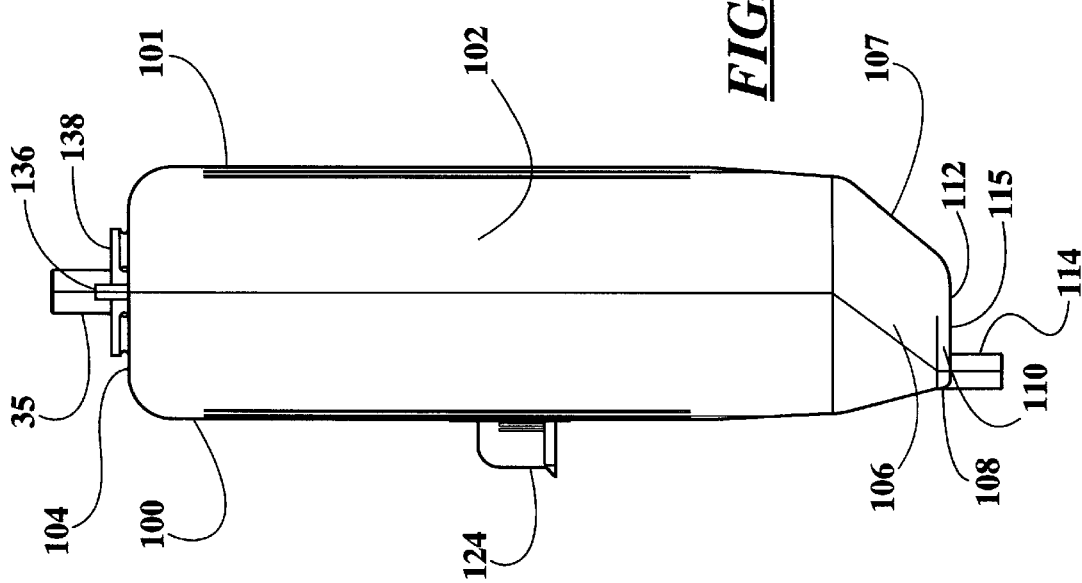
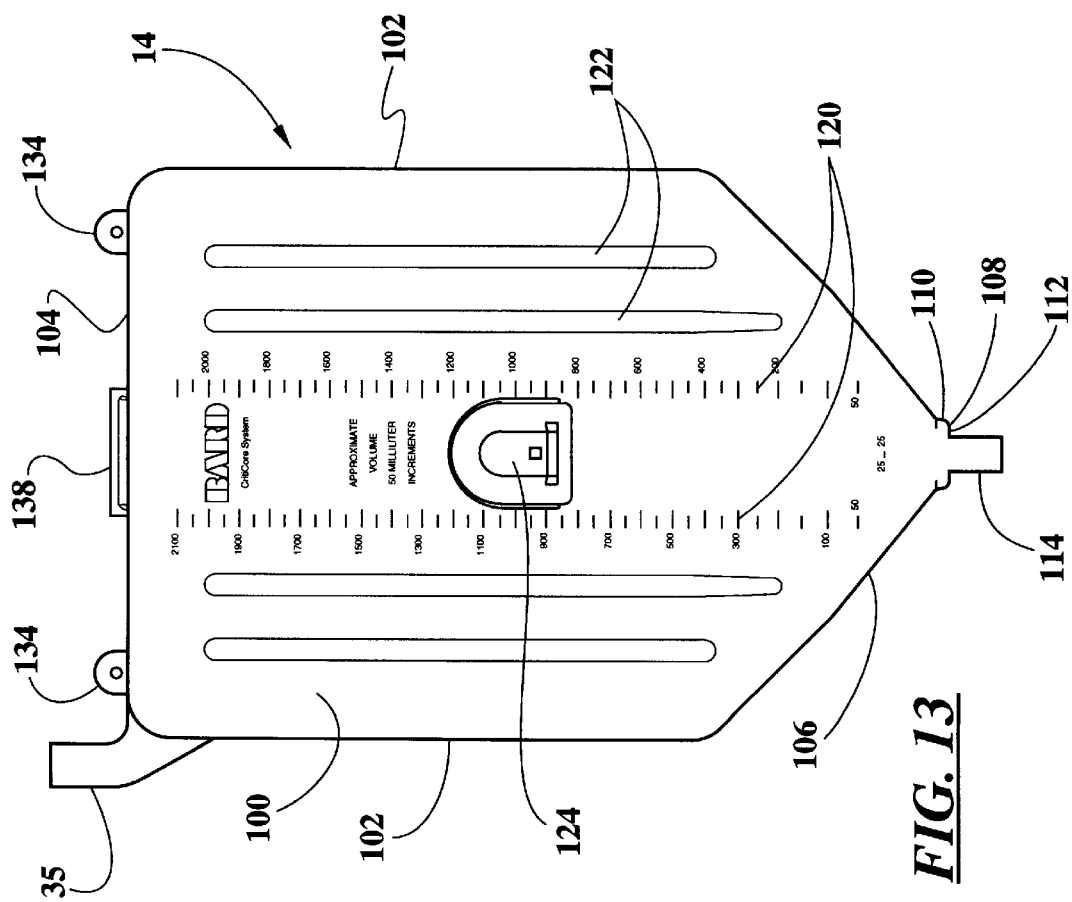

ELECTRONIC URINE MONITOR

TECHNICAL FIELD

The present invention relates generally to an apparatus for monitoring fluid output from a patient. More specifically, the invention relates to an electronic fluid output monitor which continuously measures the volume of fluid in a container by ultrasound to track a patient's fluid output.

BACKGROUND OF THE INVENTION

The importance of monitoring urine output from a critically ill patient is well known. Diminished urine output is an early sign of changing patient conditions, for example, renal failure, liver failure, or congestive heart failure. Acute changes in urine output can indicate deteriorating patient conditions even before changes in patient vital signs of blood pressure, temperature, pulse, or respiration.

In patients who are suffering renal insufficiency, bedside hemofiltration, such as continuous veno-venous hemofiltration, continuous arteriovenous hemofiltration, or peritoneal dialysis, may be required to remove ultrafiltrate (i.e. the plasma/water content of the blood). Balancing fluid input against ultrafiltrate output is crucial to maintaining proper fluid balance for the patient. Thus the importance of continuously monitoring ultrafiltrate output is well known.

Not only is monitoring the volume of fluid output crucial in the case of hemofiltration, but monitoring the rate of fluid output is equally critical. Changes in the flow rate of the ultrafiltrate output are predictive of complications such as excessive clotting of blood stopping up the hemofilter. Early warning of such clotting, as indicated by a decrease in the flow rate of the ultrafiltrate output, gives the physician the opportunity to inject heparin into the system proximal to the hemofilter to arrest clotting.

Electronic meters for continuously monitoring the fluid output of a patient are well known. Examples of typical prior art urine monitors are shown in U.S. Pat. No. 4,448,207 and U.S. Pat. No. 4,658,834. A disposable container is inserted into a reusable housing having an electronic module. Patient fluid output is discharged into the container. An ultrasound transducer is mounted to the housing adjacent the container and is acoustically coupled to a wall of the container. When the sound wave hits the interface between the air and the liquid in the container, the signal is reflected. The return signal from the ultrasound transducer is input into the electronic module, which continuously monitors the contents of the container for volume changes. In addition the electronic module continuously monitors a sensor located in a Foley catheter for changes in temperature. The device displays patient information such as volume and rate of patient fluid output on a display panel located at the upper end of the housing.

Because electronic monitors of the types disclosed in the aforementioned U.S. Pat. No. 4,448,207 and U.S. Pat. No. 4,658,834 rely on reflection of sound waves off of the air/liquid interface, these monitors encounter difficulties if the monitor is tilted from vertical. If the monitor is tilted, the air/liquid interface is no longer at a redefined angle relative to the axis of propagation of the sound waves, and the reflected signal returns at an undesirable angle. Consequently the signal received by the transducer is weak, sometimes too weak to register. This problem is exacerbated if a foreign substance is present, e.g. blood in the urine, as such substance will further attenuate the return signal.

Thus there is a need for an electronic fluid output monitor which provides accurate readings even when the monitor is tilted from vertical.

There is a further need for an electronic fluid output monitor which provides accurate readings even when a foreign substance such as blood exists in the patient's fluid output.

Another problem inherent in fluid output monitors of the type disclosed in the aforementioned U.S. Pat. No. 4,448,207 and U.S. Pat. No. 4,658,834 is that such monitors are incapable of accurately measuring small volumes of liquid. Because the depth of the liquid in the container is extremely shallow as patient fluid output is first introduced into the container, and because the liquid may not initially uniformly fill the container as a result of the effects of surface tension, prior art electronic fluid output monitors usually cannot measure volumes of less than 5 cc of fluid.

Thus there is a need for an electronic fluid output monitor which permits measurement of small volumes of liquid.

SUMMARY OF THE INVENTION

Stated generally, the present invention comprises an improved electronic fluid output monitor for continuously measuring the volume of liquid in a container by ultrasound to track a patient's fluid output. The electronic fluid output monitor provides accurate readings even when the monitor is tilted from vertical, and even when a foreign substance is present in the fluid output, such as blood in a patient's urine. The electronic fluid output monitor of the disclosed embodiment permits measurement of even small volumes of liquid.

Stated somewhat more specifically, the present invention comprises an electronic monitor for measuring a liquid, such as urine, discharged from a patient's body. The monitor comprises a housing defining a cavity, the cavity having a floor. A substantially rigid wall container is removably positioned within the cavity, the container having a bottom wall portion supported on the floor of the cavity. The container comprises a means for introducing the discharged liquid into the interior of the container to form a pool on an interior surface of the bottom wall portion. A transducer is mounted in the floor of the housing and engages the bottom wall portion of the container. Periodically the transducer is engaged to transmit energy through the bottom wall portion of the container and the pool of liquid in the container. The monitor includes a flight count means for determining the time duration required for the transmitted energy to travel from the transducer means to the upper surface of the pool and back again.

In a first aspect of the invention, the monitor comprises an optical sensor mounted on the housing which projects a beam of light into the cavity and detects any reflected light beam. The container comprises a reflective surface disposed to reflect the projected light beam back toward the sensor. If a reflected beam is not detected, an alert is displayed to signify that a container is not properly positioned within the cavity. In the disclosed embodiment the optical sensor is located on a hinged lid at the upper end of the housing, and the reflective surface of the container is the central portion of a cap fitted over an opening. A reflected beam will be detected only if a container is positioned within the cavity of the housing and the lid of the housing is properly closed.

In another aspect of the invention, a channel is formed in the floor of the housing. An outlet tube is located on the bottom wall portion of the container and projects through the channel. The contents of the container can thus be completely discharged without having to tilt the container.

In still another aspect of the invention, the monitor comprises a means responsive to the flight count means for determining the volume of fluid introduced into the container during a predetermined period of time, the duration of the predetermined period of time being selectable by a user from among a plurality of predefined durations.

Yet another aspect of the invention concerns a well formed in the lower portion of the container. The well has substantially vertical walls and a relatively narrow cross-sectional area, and the container is configured to direct the initial volume of liquid introduced into the container into the well. Thus even small amounts of liquid in the container are concentrated directly above the transducer, permitting the monitor to accurately measure small quantities of liquid.

Another aspect of the invention concerns a transducer driving routine comprising means for varying the output signal strength at which the transducer is driven to operate. Under normal operating conditions the transducer will operate at a lower of two output levels. However, if the monitor is tilted or some other condition arises which causes the return signal to be too weak to provide an accurate reading, the transducer driving system will boost its output to a higher of two output levels. Since the output signal is stronger, the reflected signal will be correspondingly stronger, such that the return signal can be received by the transducer sufficiently clearly to provide a valid reading. In the disclosed embodiment the magnitude of the output signal is a function of the duration of the charge time, and switching between the lower and higher levels of output signals is accomplished by increasing the charge time.

These and other aspects of the present invention will be explained hereinbelow in conjunction with the detailed description of the disclosed embodiment.

Thus it is an object of the present invention to provide an improved electronic fluid output monitor for continuously measuring the volume of fluid output in a container by ultrasound to track a patient's fluid output.

It is another object of the present invention to provide an electronic fluid output monitor which provides accurate readings even when the monitor is tilted from vertical.

Still another object of the present invention is to provide an electronic fluid output monitor which provides accurate readings even when a foreign substance is present in the fluid output, such as blood in a patient's urine.

Another object of the present invention is to provide an electronic fluid output monitor which permits accurate measurement of small volumes of fluid.

Other objects, features, and advantages of the present invention will become apparent upon reading the following specification, when taken in conjunction with the drawings and the appended claims.

BRIEF DESCRIPTION OF THE DRAWINGS

FIG. 6A is a side view of the pivot end of a hanger arm of the hanger component shown in FIG. 5; FIG. 6B is a cross-sectional view of the hanger arm of FIG. 6A as viewed along line 6B—6B of FIG. 6A.

FIG. 7A is a side view of the pivot end of a flange of the handle component shown in FIG. 5; FIG. 7B is a cross-sectional view of the flange of the handle of FIG. 7A as viewed along line 7B—7B of FIG. 7A.

FIG. 8A is a partial side view of the hanger and handle components showing the hanger component rotated to an intermediate position between the "down" and "up" positions;

FIG. 8B is a partial side view of the hanger and handle components of FIG. 8A showing the hanger component rotated to its "up" position and the handle rotated to a "stand-off" position in response to rotation of the hanger component.

FIG. 9 is a partial side view of the hanger and handle components showing the handle component rotated to an intermediate position between its "down" and "up" positions.

FIG. 10 is a side view of the electronic fluid output monitor of FIG. 1 showing the hangers in a raised position and the handle in a stand-off position.

FIG. 11 is a side view of the electronic fluid output monitor of FIG. 1 showing the handle in the raised position.

FIG. 13 is a front view of the disposable collection tank of the electronic fluid output monitor of FIG. 1.

FIG. 14 is a side view of the disposable collection tank of the electronic fluid output monitor of FIG. 1.

DETAILED DESCRIPTION OF THE DISCLOSED EMBODIMENT

Figure 1:
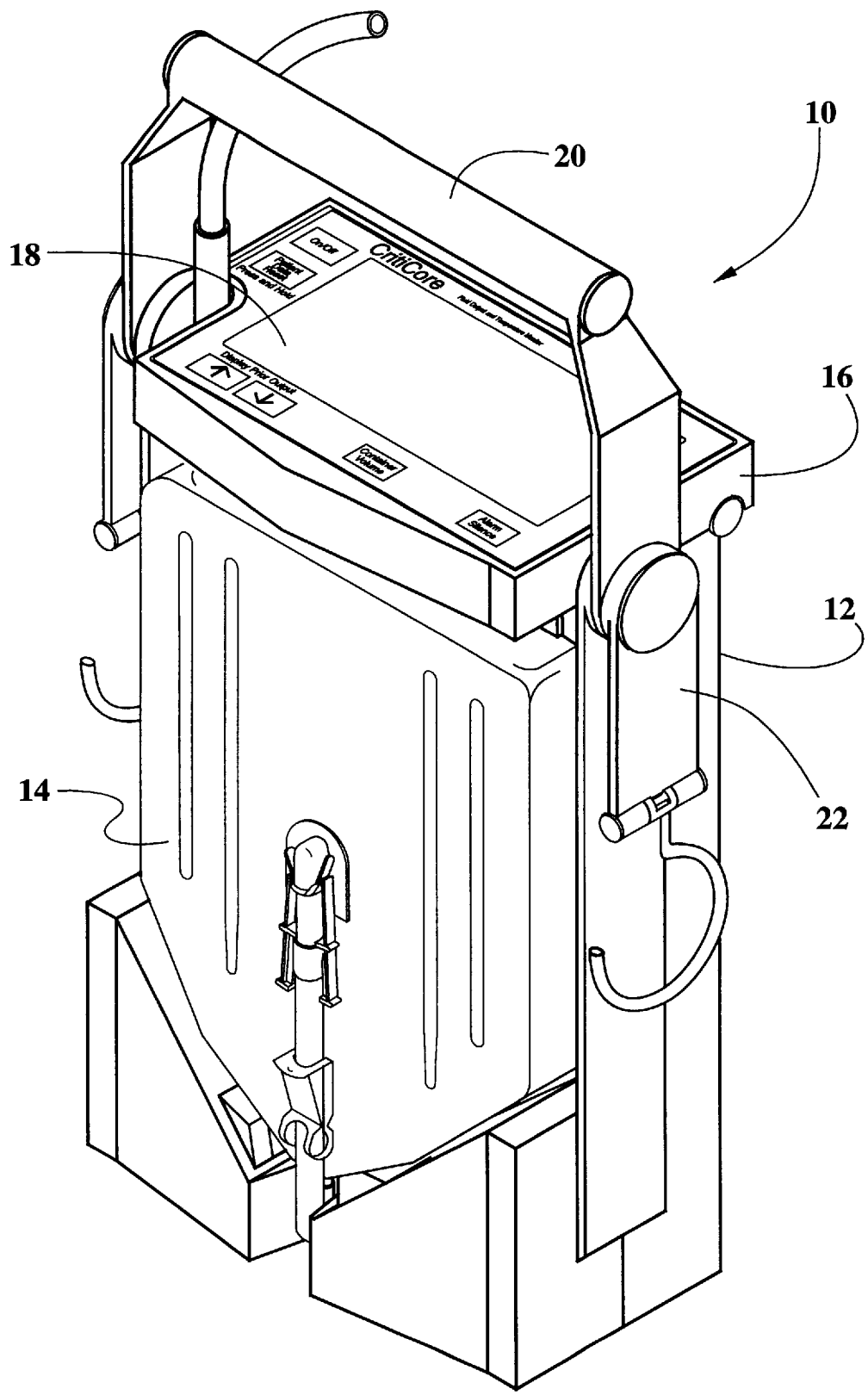
FIG. 1 is a perspective view of an electronic fluid output monitor according to the present invention.

Referring now to the drawings, in which like numerals indicate like elements throughout the several views, FIG. 1 shows an electronic fluid output monitor 10 according to the present invention. The fluid output monitor 10 is disclosed in conjunction with its use as a urine output monitor, though it will be understood that the monitor 10 can be used to monitor other types of patient fluid output, including but not limited to ultrafiltrate output resulting from hemofiltration.

The urine monitor 10 comprises a housing 12 and a disposable container 14 removably contained within the housing 12. The housing 12 has a hinged lid 16 at its upper end. A control panel 18 is located on the upper surface of the lid 16. Preferably the lid 16 is angled forward when closed to facilitate viewing of the control panel 18 from in front of the monitor 10.

A handle assembly 20 and a pair of hanger assemblies 22 are pivotally mounted to the housing 12 adjacent its upper end. The handle assembly 20 provides a means by which the monitor 10 can be carried, while the hanger assemblies 22 provide a means by which the monitor can be suspended during use. The structure and operation of the handle assembly 20 and hanger assemblies 22 will be more fully explained below.

Figure 2:
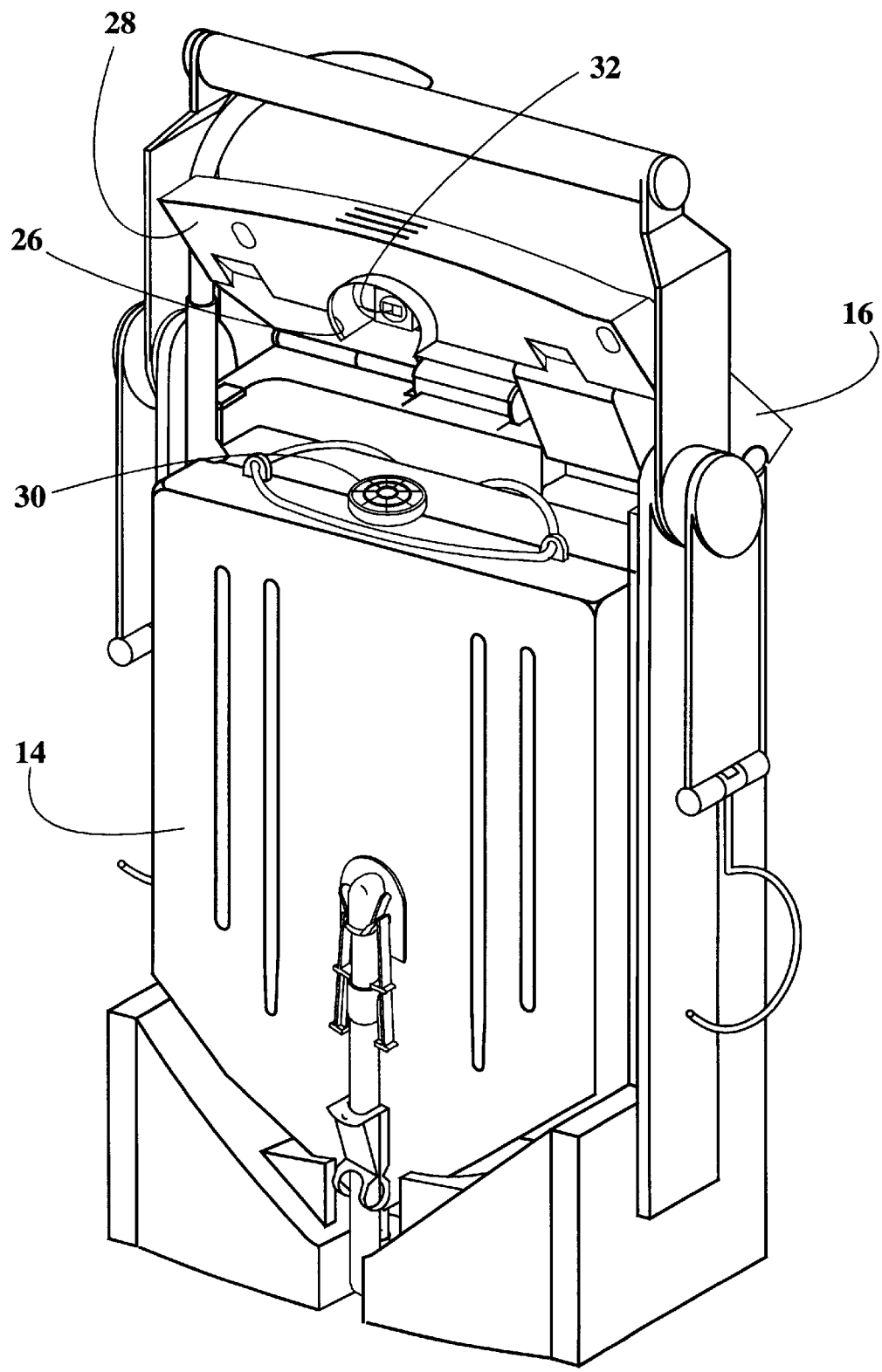
FIG. 2 is a perspective view of the electronic fluid output monitor of FIG. 1 showing the lid in a raised position.
Figure 3:
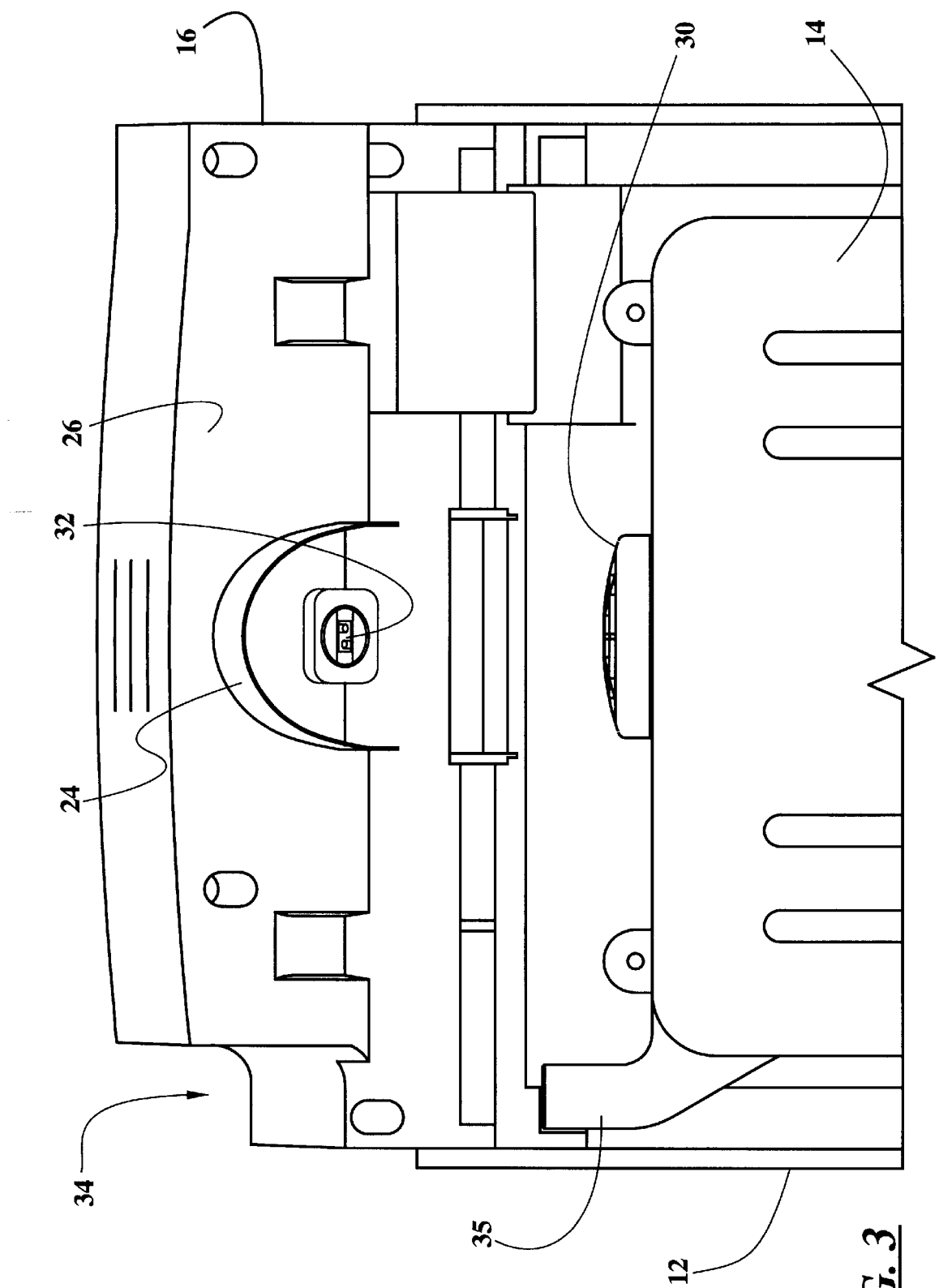
FIG. 3 is a front view of the upper portion of the electronic fluid output monitor of FIG. 1 showing the lid raised and the container in position.

Referring now to FIGS. 2 and 3, the lid 16 has an arcuate collar 24 formed on its lower surface 26. A vented cap 30 is located atop the disposable container 14. The collar 26 is configured to snugly engage the vented cap 30 when the lid 16 is lowered, centering the container 14 in an upright orientation and retaining the container within the housing 12. An optical sensor 32 is located within the collar 24. The optical sensor 32 directs a light beam downward and at an angle. If the lid 16 is closed and if a cap 30 is located within the collar 24 formed on the lower surface 26 of the lid, the reflected light beam will be detected. Otherwise, the absence of a detected return light beam will prevent the monitor 10 from misinterpreting echoes as a valid volumetric measurement and displaying an erroneous reading.

Also illustrated in FIG. 3, the lid 16 has a cutout 34 formed along its left edge, which clears an upstanding inlet port tube 35 at the upper left edge of the disposable container 14 when the lid is closed. The structure and function of the inlet port tube 35 will be more fully explained below in conjunction with the description of the disposable container 14.

Figure 4:
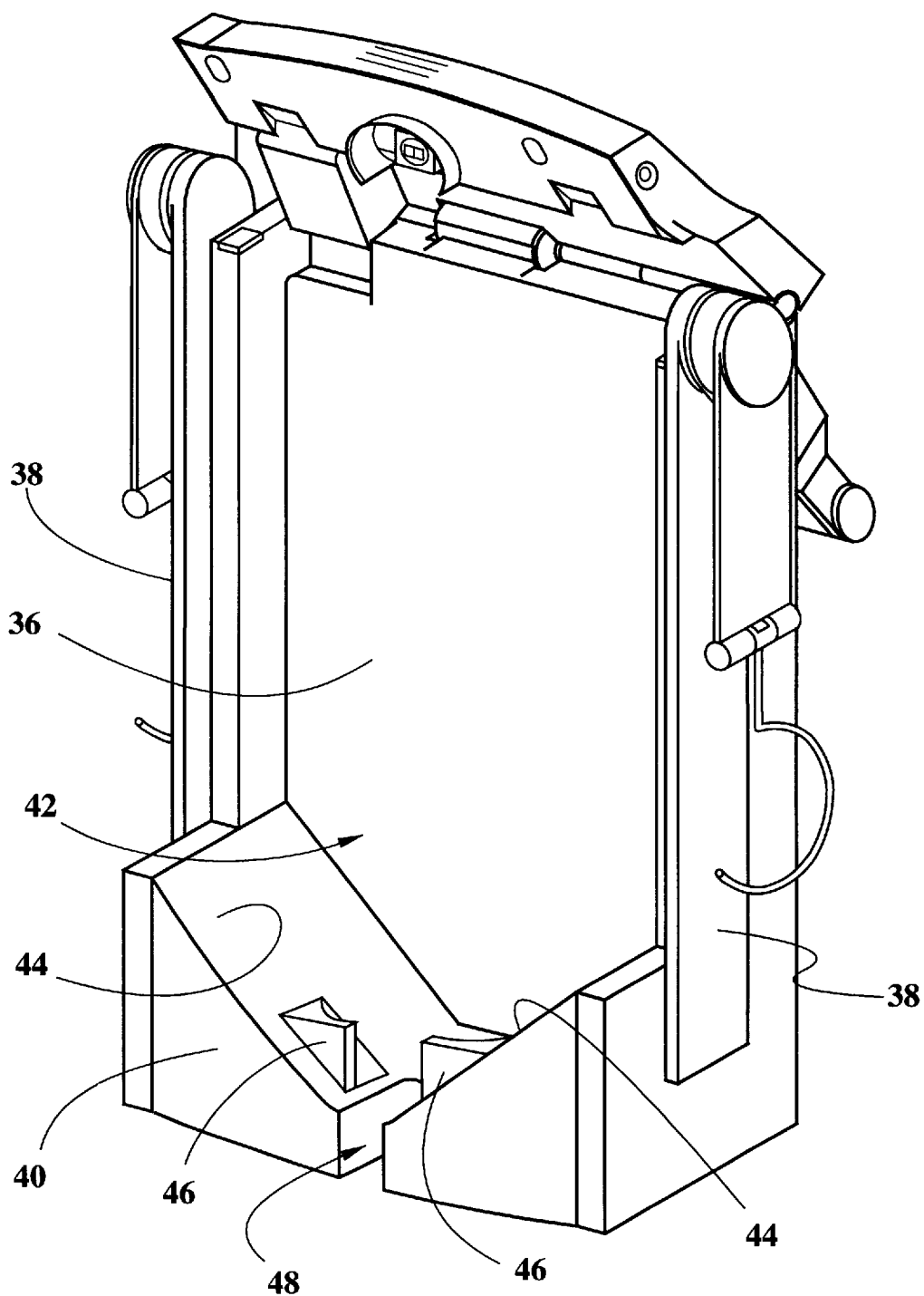
FIG. 4 is a perspective view of the electronic fluid output monitor of FIG. 1 showing the disposable container removed.
Figure 5:
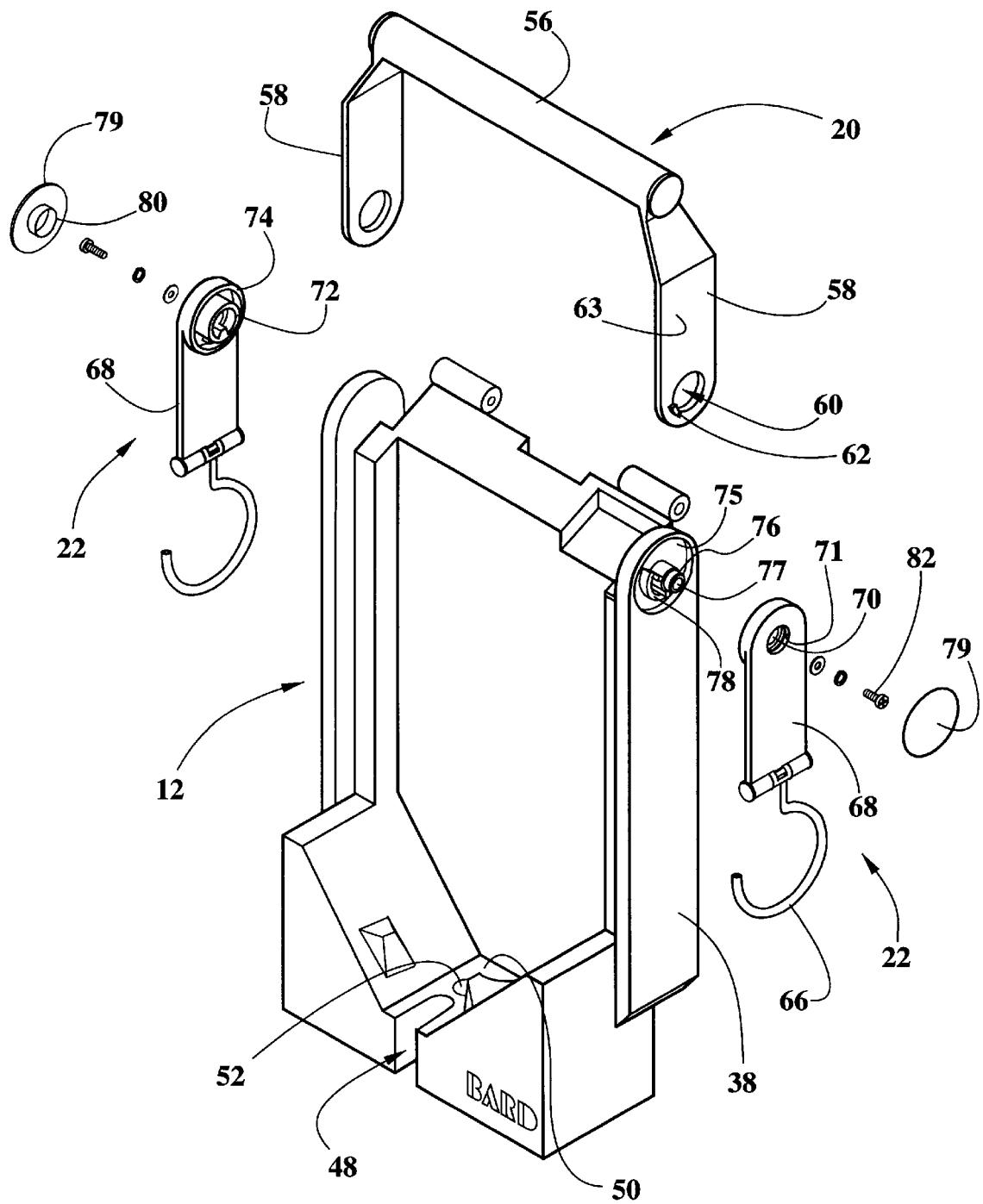
FIG. 5 is a perspective view of the electronic fluid output monitor of FIG. 1 with the lid and container removed and showing the hanger and handle components exploded away from the housing.

Referring now to FIG. 4, the housing 12 comprises a back panel 36, opposed side panels 38, and a lower portion 40, all of which define a cavity 42. The cavity 42 includes angled lower walls 44 which converge at their lower ends. An upstanding stop member 46 is formed on each of the angled lower walls 44. A channel 48 is formed in the front of the lower portion 40 and extends approximately half the depth of the housing 12. As can be seen in FIG. 5, a floor 50 is formed at the base of the cavity 42, and an ultrasound transducer 52 is mounted on the floor 50 adjacent the rearward terminus of the channel 48.

FIGS. 5–11 illustrate the handle assembly 20 and hanger assemblies 22. Referring first to FIG. 5, the handle assembly 20 comprises an elongated cylindrical handle 56 with brackets 58 depending downward from each end. Each bracket 58 has a smooth through bore 60 formed at the end of the bracket which is opposite the end attached to the handle 56. A key 62 projects outward from the exterior face 63 of each bracket 58 at the forward edge and slightly below center of the corresponding bore 60.

Each of the hanger assemblies 22 comprises a hook 66 pivotally mounted to a corresponding arm 68. The hook 66 proscribes an arc of approximately 270° and is adapted to engage, for example, the rail of a hospital bed or the like. Each of the arms 68 includes a through bore 70 formed adjacent the end opposite the hook 66. A concentric counterbore 71 is formed at the outer end of each bore 70. An inner annular flange 72 and an outer annular flange 74 project from the inner face of each arm 68 concentric with the bore 70, the inner annular flange 72 extending beyond the outer annular flange 74.

Still referring to FIG. 5, a circular recess 75 is formed adjacent the upper end of each side panel 38. An outwardly projecting post 76 is located at the center of each circular recess 75. The end of the post 76 has a threaded bore 77 formed therein. An arcuate flange 78 is formed within the circular recess 75 on each side panel 38 adjacent to the corresponding post 76. A decorative cap 79 has an inwardly projecting annular flange 80 formed on its inner surface.

The brackets 58 of the handle assembly 20 fit over the posts 76 on the side panels 38 of the housing 12. The hanger assemblies 22 then fit over the posts 76 on the outside of the flanges 58 of the handle assembly 20. The inner annular flanges 72 on the arms 68 of the hanger assemblies 22 fit within the bores 60 in the brackets 58 of the handle assembly 20. The threaded shank of a screw 82 is then inserted through the bore 70 in the arm 68 of the hanger assembly 22, through the hole 60 in the bracket 58 of the handle assembly 20, and threaded into the bore 77 in the end of the corresponding post 76 on the side panel 38. The head of the screw 82 and associated washers fit within the counterbore 71 at the outer end of each bore 70 and engage the base of the counterbore to retain the hanger assembly 22 on the corresponding post 76. The inwardly projecting annular flange 80 on the interior surface of the decorative cap 79 then fits snugly into the counterbore 71 over the head of the screw 82 to conceal the screw.

The pivot end 83 of an arm 68 of a hanger assembly 22 is shown in FIGS. 6A and 6B. The arm 68 of each hanger assembly 22 includes a bearing 84 mounted within the through bore 70. A tooth 85 extends radially inward from the bore wall at the bottom of the through bore 70. An arcuate tab 86 is formed along the lower edge of the inner annular flange 72.

The pivot end 88 of a bracket 58 of the handle assembly 20 is shown in FIGS. 7A and 7B. The bracket 58 includes a tooth 90 formed on the wall of the bore 60 at the six o'clock position as shown in FIG. 7A and extending radially inward. The key 62 on the exterior face 63 of the bracket 58 is located at approximately the eleven o'clock position with respect to the bore 60 as shown in FIG. 7A.

FIGS. 8–11 illustrate the interaction between the handle 20 and hook assemblies 22. With the handle 20 and hook assemblies 22 installed onto the housing 12, the inner annular flange 72 projecting inward from the arm 68 of the hook assembly 22 fits within the smooth through bore 60 of the bracket 58 of the handle assembly 20. The outward projecting key 62 on the exterior face 63 of the bracket 58 of the handle assembly is disposed within an annular recess 92 defined between the inner and outer annular flanges 72, 74.

With reference first to FIG. 8A, the handle assembly 20 and hook assembly 22 are normally in a "down" or storage position. The hook assembly 22 can be rotated only in a clockwise direction as seen in FIG. 8A, as the tooth 85 formed on the arm 68 will confront the arcuate flange 78 on the side panel 38 of the housing 12 (see FIG. 5) to prevent the hook assembly from rotating in a counterclockwise direction. When the hook assembly 22 is rotated approximately 90° in a clockwise direction, the arcuate tab 86 formed along the lower edge of the inner annular flange 72 of the arm 68 confronts the key 62 on the exterior face 63 of the bracket 58 of the handle assembly 20. As is shown in FIG. 8B, further rotation of the hook assembly 22 in a clockwise direction will cause a corresponding clockwise rotation of the handle assembly 20. When the hook assembly 22 has reached its full upright position, as shown in FIG. 10, the handle assembly 20 projects rearward of the housing 12 substantially horizontally.

Referring now to FIG. 9, the handle assembly 20 is prevented from rotating in a counterclockwise rotation because the tooth 90 formed on the wall of the bore 60 of the bracket 58 will confront the arcuate flange 78 on the side panel 38 of the housing 12 (see FIG. 5) to prevent the handle assembly from rotating in a counterclockwise direction. When the handle assembly 20 is rotated in a clockwise direction, the key 62 on the exterior face 63 of the bracket 58 rotates away from the arcuate tab 86 formed along the lower edge of the inner annular flange 72 of the arm 68 of the hanger assembly 22. Thus the handle assembly 20 can be raised to its full upright position, as shown in FIG. 11, without causing any rotation of the hanger assemblies 22.

The advantage of this cooperative interaction between the handle assembly 20 and the hanger assemblies 22 is that whenever the hanger assemblies 22 are used to suspend the monitor 10 from a structure, e.g., a patient bed, the handle assembly 20 automatically moves into a "standoff" position in which the handle isolates the monitor from lying flat against the side of the bed. This mechanism allows the monitor 10 to pivot to vertical position so as not to interfere with the ultrasound measuring function.

Figure 12:
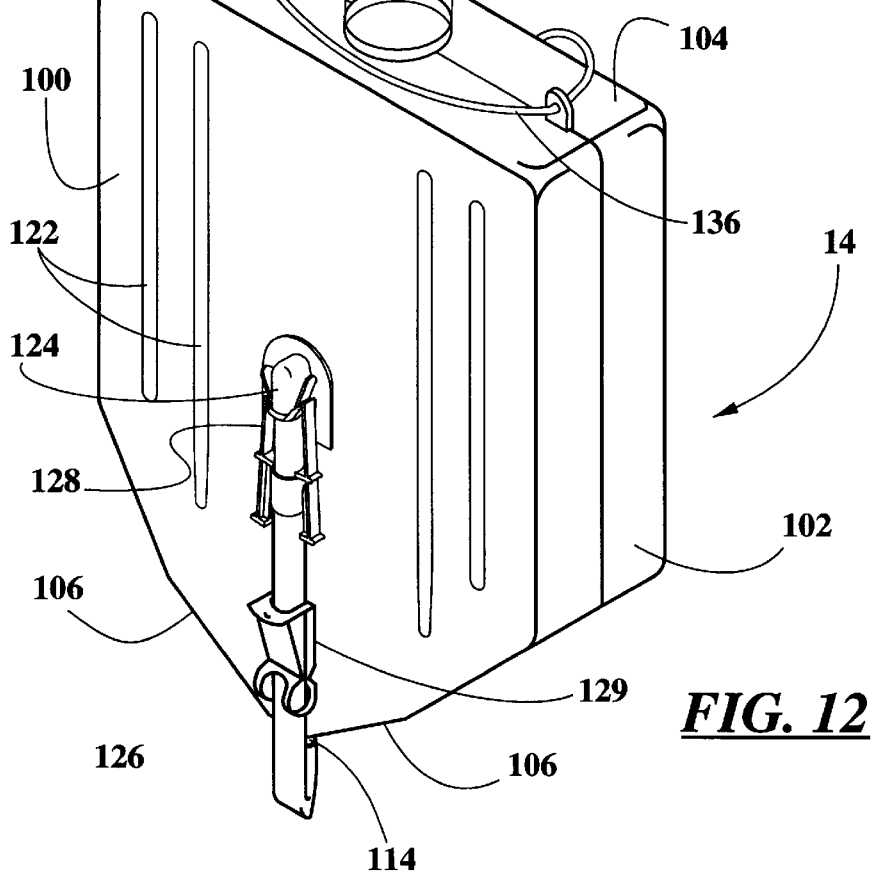
FIG. 12 is a perspective view of the disposable collection tank of the electronic fluid output monitor of FIG. 1.

FIGS. 12–14 illustrate the disposable container 14. The container 14 is preferably comprised of a transparent, substantially rigid plastic and includes a front panel 100, rear panel 101, side panels 102, and a top panel 104. Sloping lower side walls 106 and a forward sloping lower rear wall 107 extend downward from the side panels 102 and rear panel 101 respectively and converge at a well 108. The well 108 includes vertical side walls 110 and a flat base 112. An outlet port 114 extends downward from the base 112 of the container 14 proximate to the forward end of the base. The flat, uninterrupted rear portion 115 of the base 112 comprises a transducer-engaging surface, as will be more fully explained below.

The front panel 100 of the container 14 includes graduated markings 120 in units of milliliters by which the volume of fluid in the container 14 can be visually determined. A plurality of vertical ribs 122 are formed in the front and rear panels 100, 101 to enhance the rigidity of the container 14. Also on the front panel 100 is a retainer or "doghouse" 124. As shown in FIG. 12, a rubber tubing 126 has one end fitted over the outlet port 114 extending downward from the base 112 of the container 14. The free end of the rubber tubing 126 has a clip 128 mounted thereto for releasably engaging the retainer 124 on the front panel 100 of the container 14. A spring clamp 129 is also attached to the rubber tubing 126 and is selectively operative to occlude the lumen of the tubing. The retainer 124, tubing 126, clip 128, and clamp 129 are of a conventional design normally associated with urinary drainage bags, and their operation will be readily understood by one skilled in the art.

At the upper end of the container 14, the inlet port 35 extends upward. The inlet port 35 is adapted to receive the distal end of a catheter tube 132 for introducing liquid into the container 14. A pair of tabs 134 having holes therethrough extend upward from the top panel 104 of the container. A string loop 136 is threaded through the holes in the tabs 134 to provide a means for carrying the container. Finally a neck 138 extends upward from the top panel 104 of the container and is configured to be engaged by the vented cap 30. A circular filter 139 is secured across the top of the neck 138 and is protected by the vented cap 30 when the cap is installed atop the neck. In the disclosed embodiment the filter 139 is bonded to the neck 138 by heat welding, though other means for securing the filter can be used, including adhesive bonding, ultrasonic welding, or the like. Also, while the filter 139 is secured to the neck 138 of the container 14 in the disclosed embodiment, the filter 139 can alternatively be secured to the underside of the vented cap 30. In the disclosed embodiment the filter element 139 is comprised of hydrophobic Gelman Versapor 5000R, Nylon-based substrate.

Figure 15:
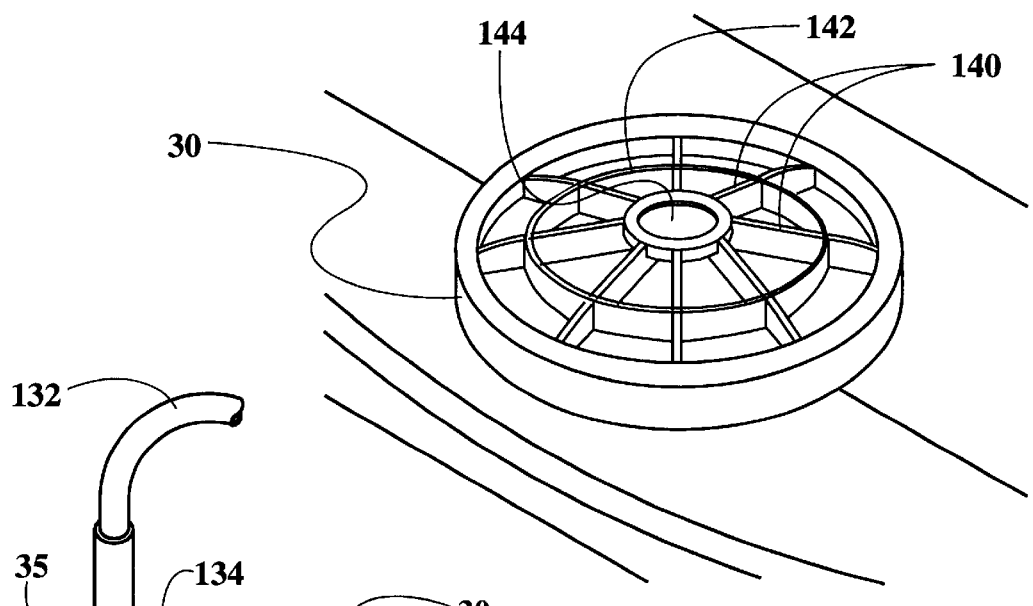
FIG. 15 is an enlarged perspective view of a vented cap for the disposable collection container of FIGS. 12–14.

Referring now to FIG. 15, the vented cap 30 comprises a series of radial ribs 140 and annular ribs 142. The pattern of the ribs 140, 142 protects the underlying filter against becoming dislodged by fingers, pens, etc., while permitting the flow of air through the cap 30. A flat portion 144 is provided at the center of the cap. This central portion 144 provides a reflective surface which interacts with the optical sensor 32, as previously described.

Figure 16:
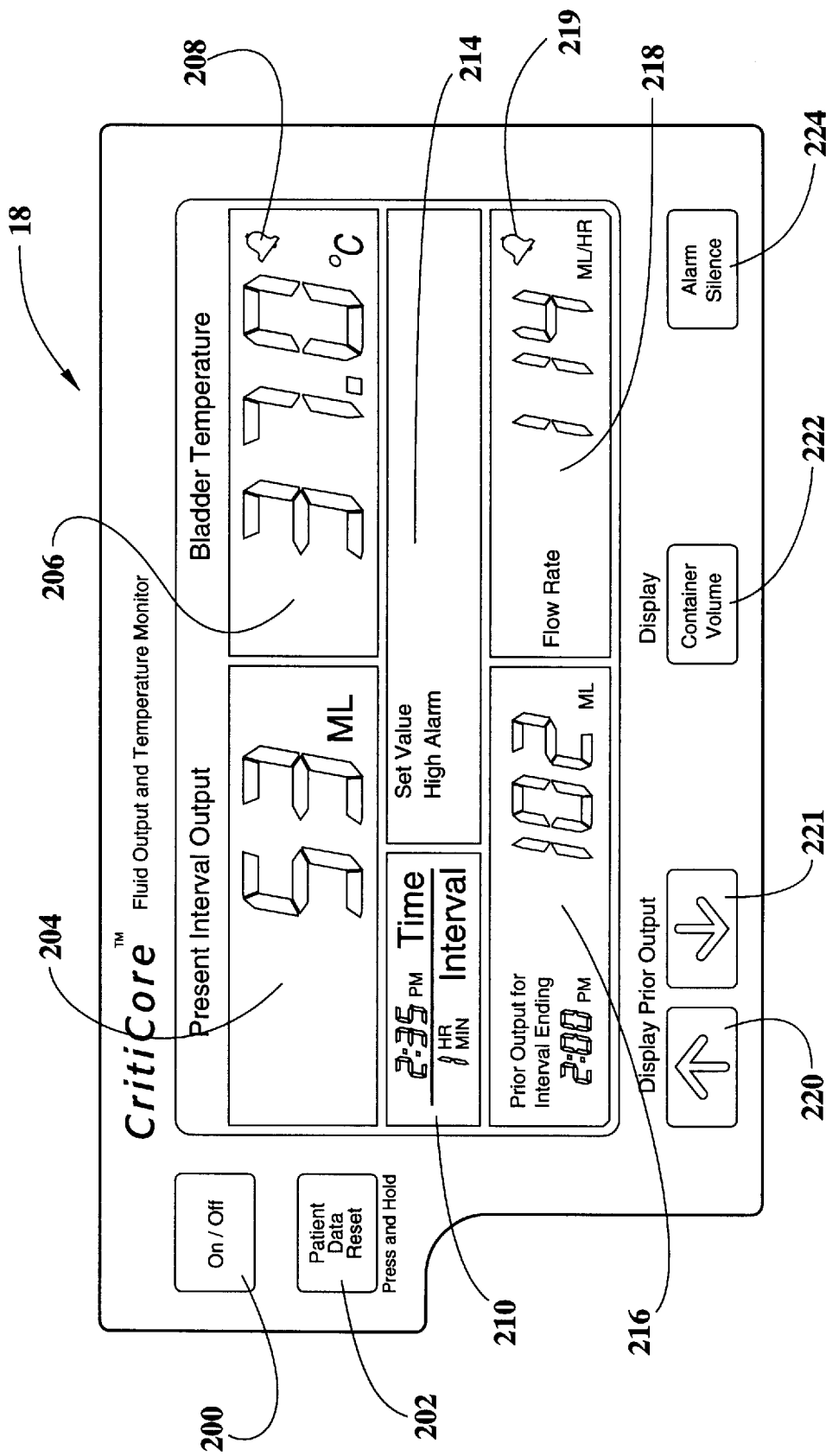
FIG. 16 illustrates the layout of the control panel which is located on the lid of the electronic fluid output monitor of FIG. 1.

FIG. 16 shows the control panel 18, which is located on the upper surface of the lid 16. In the disclosed embodiment electroluminescent backlighting is provided to enable the control panel 18 to be read in a darkened room. An on/off button 200 located in the upper left corner of the control panel 18 activates the electronic urine monitor 10. Just beneath the on/off button 18 is a patient data reset button 202 which, when pressed and held, will clear all accumulated patient data.

To the right of the patient data reset button 202 is a present interval output display 204 in which the urine output for the present time interval is continuously displayed, in milliliters per hour. In FIG. 16 the present interval output display 204 indicates that 53 milliliters of urine have been output in the present time interval.

To the right of the present interval output display 204 is a bladder temperature display 206, in which the measured bladder temperature is displayed in either °F. or °C. In FIG. 16 the bladder temperature display 206 indicates a bladder temperature of 37.0° C. In the disclosed embodiment the temperature is measured by a thermistor temperature sensor of conventional design, which is located in the forward end of the Foley catheter. However, it will be appreciated that other types of temperature sensors, such as thermocouples or RTDs, can be used. The temperature sensor interfaces with the electronic urine monitor 10 by means of a jack (not shown) which is located on an edge of the lid 16 into which a plug associated with the temperature sensor is inserted. A bell-shaped alarm symbol 208 appears in the upper right-hand corner of the bladder temperature display 206 when the bladder temperature alarm is enabled.

Beneath the present interval output display 204 is a time interval display 210. An upper portion of the time interval display 210 shows the present time, in either 12-hour (AM/PM) or 24-hour (military) format. A lower portion of the time interval display 210 exhibits the duration of the time interval. In the disclosed embodiment, the duration of the time interval can be set for 5, 10, 15, 20, or 30 minutes or for 1 or 2 hours. This lower portion of the time interval display 210 comprises a two-digit numeric display in combination with indicia indicating hours or minutes. In FIG. 16 the time is displayed in 12-hour format as 2:35 PM, and the selected time interval is 1 hour.

To the right of the time interval display 210 is a display 214 in which various user interface and alert messages are displayed as appropriate. In the disclosed embodiment the user interface messages include (a) set value; (b) high alarm; and (c) low alarm. These user interface messages are displayed when user-defined parameters are being set by the operator, as will be explained below. In addition, the user interface messages "high alarm" and "low alarm" are displayed when an alarm condition exists, to notify the operator whether the measured parameter which is the subject of the alarm condition exceeds or falls below predefined parameters. The alert messages in the disclosed embodiment are: (a) check container; (b) not level; (c) full container; (d) check probe; (e) low battery; and (f) alarm silenced. When any of these conditions exist, the associated alert message will be displayed on the user interface and alert message display 214, optionally in conjunction with an audible alarm. In FIG. 16, the user interface and alert message display 214 is displaying the "set value" and "high alarm" messages, which indicate that a user-defined parameter is being set, and that the parameter being set is the "high alarm" limit.

Beneath the time interval display 210 is a display 216 showing output for a prior time interval. The left portion of the display 216 shows the ending time of the interval for which output is being displayed, in either 12- or 24-hour format. The right portion of the display 216 shows the output for the selected time interval, displayed in milliliters. In FIG. 16, the display 216 indicates that the selected time interval ended at 2:00 PM; and for that interval, 102 milliliters of urine were output.

To the right of the selected interval display 216 is a display 218 which shows the patient's output flow rate, in milliliters/hour. A bell-shaped alarm symbol 219 is displayed in the upper right corner of the display 218 whenever a patient output flow rate alarm is enabled. In its default mode, the display 218 will either continuously display the output flow rate or will be blank, depending upon user-defined settings. In other modes of operation the display 218 will display container volume, in milliliters; or cumulative output, in milliliters. As used herein, the term "cumulative output" will be understood to mean the sum of all of the previous interval outputs from the prior interval displayed in the selected prior interval display 216 up to and including the most recent prior interval. The left side of the display 218 comprises indicia indicating whether flow rate, container volume, or cumulative output is being displayed; the right side of the display 218 includes a four-digit numeric display.

Below the selected interval display 216 at the bottom left of the control panel 18 are up- and down-arrow keys 220, 221 by which the operator interfaces with the control panel 18. In the normal operating condition, pressing the up-arrow key 220 causes the selected time interval to increment by one selected interval, and pressing the down-arrow key 221 causes the selected time interval to decrement by one selected interval. When the most recent prior time interval is the selected interval, pressing the up-arrow key 220 causes the display to "wrap" around to the earliest time interval. Similarly, if the earliest prior time interval is the selected interval, pressing the down-arrow key 221 causes the display to "wrap" around to the most recent prior time interval. As the selected time interval is revised, the displays 216, 218 are automatically updated to reflect the appropriate values. Thirty seconds after the last press of the up- or down-arrow keys 220, 221, the displays 216, 218 revert to their default modes.

At the bottom center of the control panel 18 is a container volume button 222. Pressing the button 222 will cause the display 218 to reflect the total volume of fluid in the container 14. Thirty seconds after the button 222 is released, the display 218 will revert to its default mode. To the right of the container volume button 222 is an alarm silence button 224, which the operator can press to silence an audible alarm.

Figure 17:
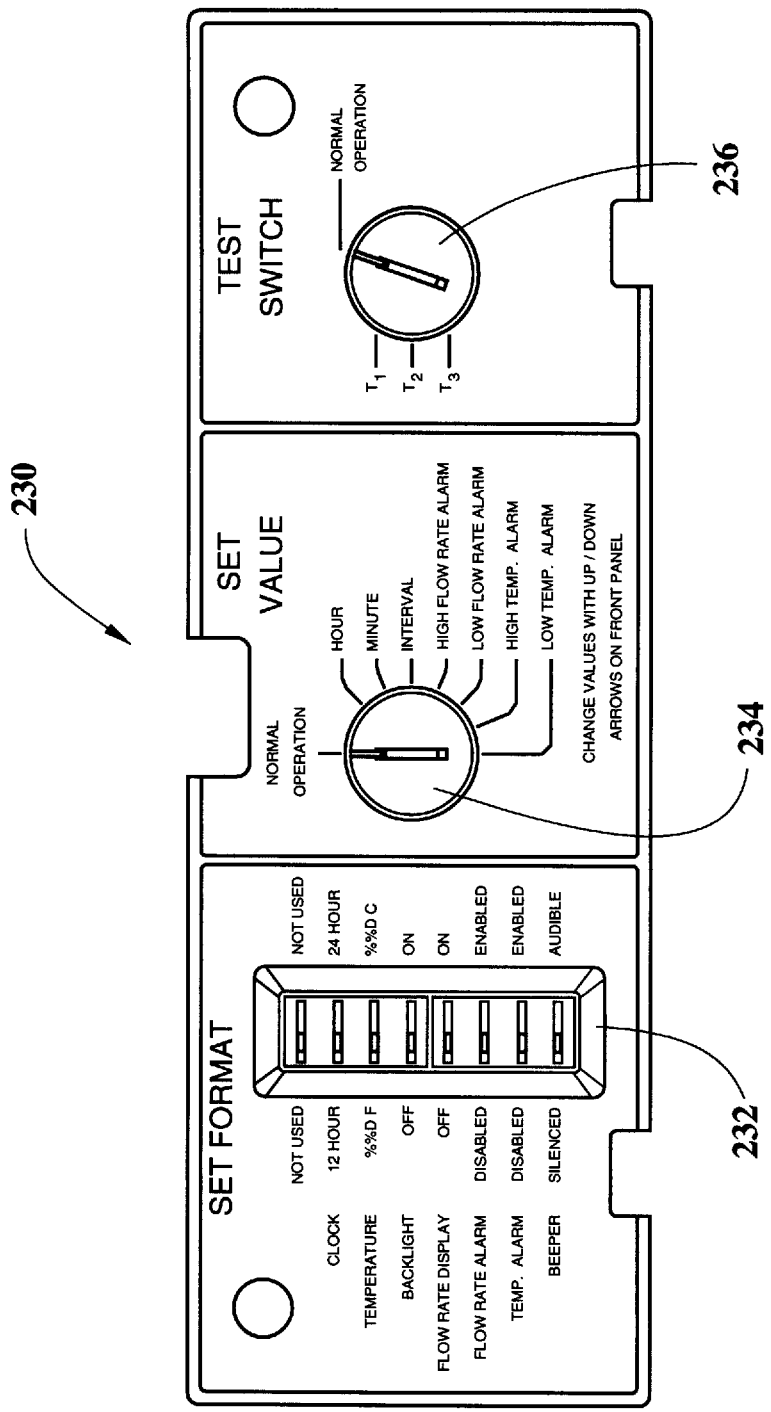
FIG. 17 is an elevation view of the back panel of the electronic fluid output monitor of FIG. 1.

FIG. 17 illustrates a switch panel 230 by which user-defined settings are controlled. The switch panel 230 is located behind a hatch at the rear of the housing 12. At the left side of the switch panel 230 is a bank 232 of eight DIP switches. These DIP switches control whether the clocks in the displays 210, 216 of the control panel 18 are displayed in 12- or 24-hour format; whether the bladder temperature in the display 206 is shown in degrees Celsius or degrees Fahrenheit; whether a backlight for the control panel 18 is on or off; whether the flow rate is normally displayed in the display 218, whether the flow rate and bladder temperature alarms are enabled or disabled; and whether the audible alarm is enabled or disabled.

In the central portion of the switch panel 230 is a rotary switch 234 which is used in combination with the up- and down-arrow keys 220, 221 on the control panel 18 to enter various settings. When the rotary switch 234 is in its "normal operation" position, the up- and down-arrow keys 220, 221 are operative to increment or decrement the prior time interval for which patient data is displayed. When the rotary switch 234 is in its "hour" or "minute" positions, the up- and down-arrow keys 220, 221 are used to set the system clock, as shown in the time interval display 210. When the rotary switch 234 is in its "interval" position, the up- and down-arrow keys 220, 221 permit the operator to set the desired interval of time for which the monitor will track fluid output data. When the rotary switch 234 is in the "high flow rate alarm" or "low flow rate alarm" positions, the up- and down-arrow keys 220, 221 permit the operator to select the upper and lower limits at which the flow rate alarms will actuate. And finally, when the rotary switch 234 is in the "high temp alarm" or "low temp alarm" positions, the up- and down-arrow keys 220, 221 permit the operator to select the upper and lower bladder temperatures at which alarms will actuate.

The right-hand portion of the switch panel 230 includes another rotary switch 236 which invokes various test modes for diagnostic purposes.

Use of the control panel 18 and switch panel 230 to set a user-defined parameter will now be explained. The operator first turns the rotary switch 234 until the indicator stripe on the switch dial is aligned with the indicia corresponding to the parameter which the operator wishes to set. For example, if the operator wishes to set the time, the rotary switch 234 is turned to the "hour" position; the "hour" segment of the time readout in the upper portion of the time interval display 210 will then begin to flash; concurrently the "set value" message in the user interface and alert message display 214 begins to flash. The operator then uses the "up arrow" and "down arrow" keys 220, 221 to set the clock to the correct "hour" setting. The rotary switch 234 is then turned to the "minute" position; the "minutes" segment of the time readout in the upper portion of the time interval display 210 will then begin to flash, and the "set value" message continues to flash in the display 214. The operator then uses the "up arrow" and "down arrow" keys 220, 221 to set the clock to the correct "minutes" setting, and the rotary switch 234 is returned to the "normal operation" position.

Similarly, to set the "high flow rate alarm," the operator turns the rotary switch 234 to the "high flow rate alarm" position; the messages "set value" and "high alarm" will flash in the display 214, and the present value for the high flow rate alarm will flash in the output flow rate display 218. The operator uses the "up arrow" and "down arrow" keys 220, 221 to step forward or backward until the desired new high flow rate limit is displayed. Similar steps are followed to set the "low flow rate alarm," the "high temperature alarm," and the "low temperature alarm." When all settings are complete, the operator returns the rotary switch 234 to the "normal operation" setting.

Prior art electronic urine monitors experience problems acquiring accurate readings when the monitor is tilted from vertical. When the monitor is not vertical, the air-fluid interface is angled with respect to the axis of propagation of the sound waves such that the return signal is reflected off-axis. The transducer thus may not acquire a sufficiently strong return signal to register an accurate reading. On the other hand, if such a prior art electronic urine monitor were to employ a transducer which generates a stronger pulse, then spurious return signals, for example off the top wall of the container, can cause false readings.

To overcome this problem, the electronic urine monitor 10 of the present invention employs a transducer 52 which is driven to operate at either of two signal strengths. Stated broadly, under normal operating conditions the transducer 52 will operate at a lower of two output levels. However, if the monitor 10 is tilted or some other condition arises which causes the return signal to be too weak to provide an accurate reading, the transducer driving system will boost its output to a higher of two output levels. Since the output signal is stronger, the reflected signal will be correspondingly stronger, such that the return signal can be received by the transducer 52 sufficiently clearly to provide a valid reading. In the disclosed embodiment, the higher strength output signal is approximately twice as strong as the lower strength output signal. In the disclosed embodiment the magnitude of the output signal is a function of the duration of the charge time, and switching between the lower and higher levels of output signals is accomplished by increasing the charge time. However, it will be appreciated by those skilled in the art that other means for controlling the level of the output signal, such as a transformer, may be used.

Figure 18:
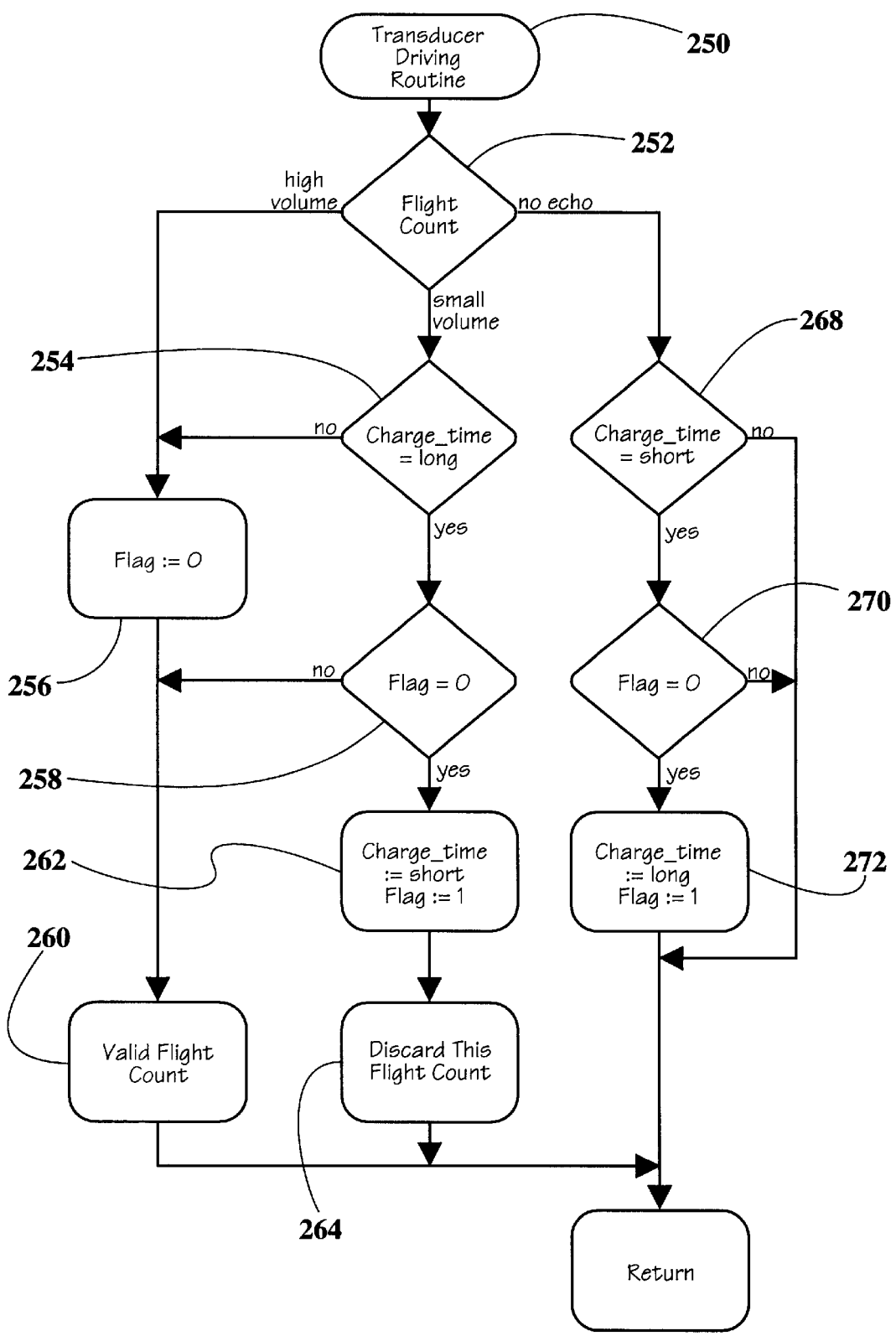
FIG. 18 is a flow diagram of the transducer driving routine of the electronic fluid output monitor of FIG. 1.

FIG. 18 shows a flow chart of a transducer driving routine 250 which is executed about four times every second. When the transducer 52 receives a return signal, the elapsed time since the output signal, or "flight count," is measured at 252. If the flight count indicates a low volume, i.e. is a short elapsed time, the routine checks at 254 to determine whether the output signal was the result of a long charge time, i.e., whether the output signal strength was high. If not, then a "weak signal" flag is set to "false" at 256. If, on the other hand, the routine determines at 254 that the output signal strength was high, then the routine checks at 258 to determine whether the "weak signal" flag is off (indicating that the output signal was strong). If not, i.e., the output signal was weak, the transducer driving routine validates the flight count at 260, and the flight count is passed on to the monitor control software (see discussion of FIGS. 20–22, below). However, if the routine determines at 258 that the "weak signal" flag was off, then the charge time is re-set to "short" and the "weak signal" flag is set to "true" at 262. The routine then discards the flight count at 264, and the routine repeats.

If the flight count at the first step 252 of the routine 250 indicates a high volume of fluid in the container, i.e. a long "flight count," 14, then the "weak signal" flag is turned off at 256, the flight count is validated at 260, and the flight count is passed on to the monitor control software.

If no echo is detected at the first step 252 of the routine 250, then the routine checks at 268 to determine whether the charge time was short, i.e., whether the output signal strength was low. If not, that is, if the output signal was strong and there is still no detectable return, this iteration of the driving routine terminates. But if the output signal strength was low, then the routine checks at 270 whether the "weak signal" flag is off. If so, the charge time is re-set to "long" and the "weak signal" flag is set to "true" at 272. Since there is no flight count to be validated or discarded, the routine repeats at this point. If the "weak signal" flag is determined at 270 to be "on," this iteration of the driving routine terminates.

The foregoing transducer driving routine 250 employs a low output signal strength, if sufficient to produce a detectable return, so that spurious reflections off of interfaces other than the liquid surface will not produce erroneous readings. On the other hand, if conditions arise under which the low output signal strength will not result in a detectable return, the transducer driving routine will boost the output signal strength to produce a detectable return.

Figure 19:
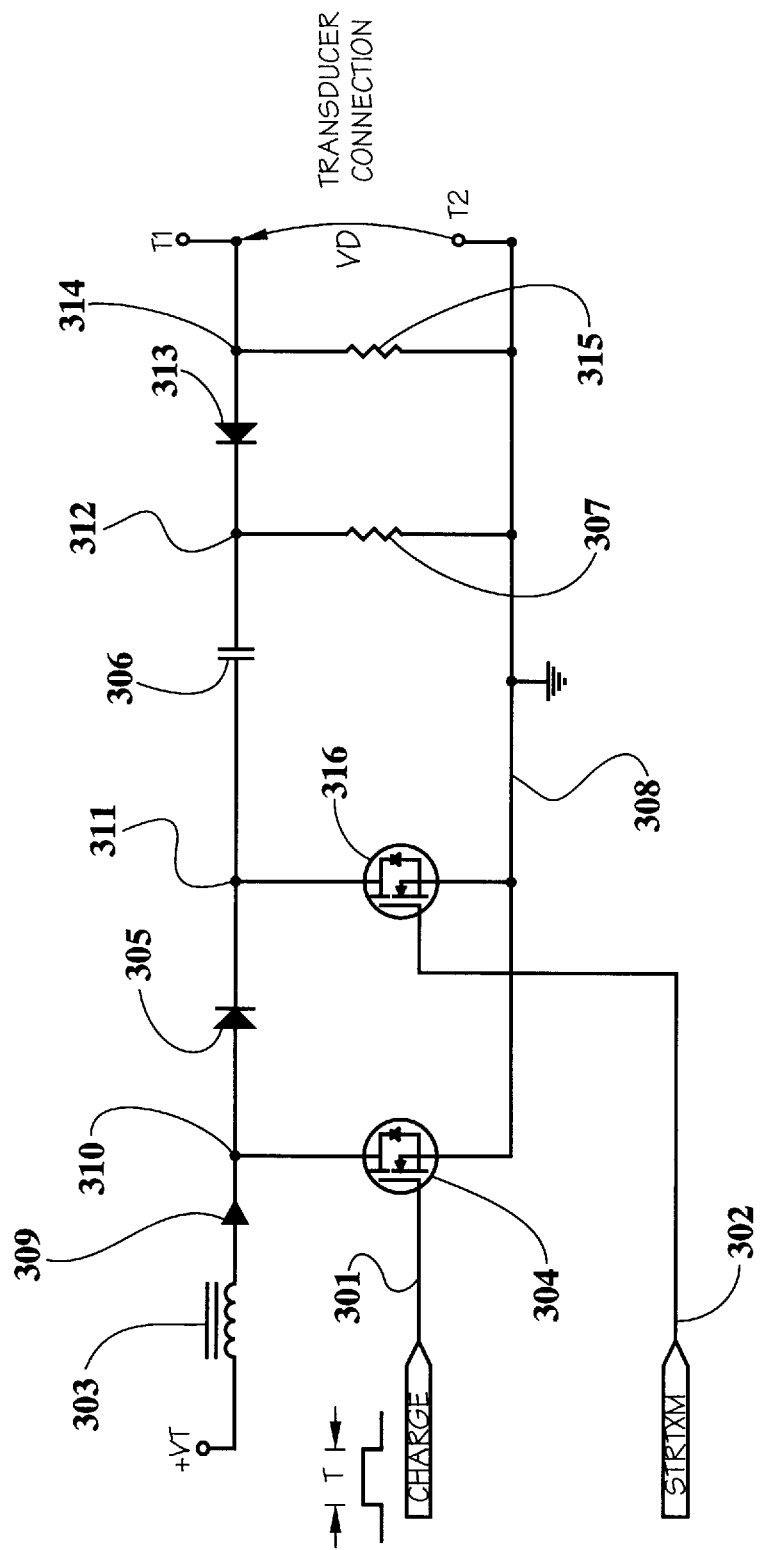
FIG. 19 is an electrical schematic of the charging system of the electronic fluid output monitor of FIG. 1.

FIG. 19 is a schematic diagram of the driver circuit 300 for the transducer 52. The driver circuit 300 steps up a pulsed voltage VT from a 6 volt power supply (not shown) to provide a high voltage VD pulse appropriate for driving the transducer. In the disclosed embodiment electrical power to the monitor 10 is supplied completely by internal batteries, eliminating the need for power cords and enhancing portability. Nominal battery life is six months under typical operating conditions. The driving voltage VD is variable to accommodate different conditions, such as a weak transducer 52, tilting of the container 14, and poor coupling between the transducer and the container 14. In the preferred embodiment, the driving voltage VD is controlled by software. The software provides three signals: a charge (CHARGE) signal on line 301; a strobe (STRTXM) signal on line 302; and the signal (not shown) which causes the pulsed voltage VT. The magnitude of the driving voltage is controlled by the duration, or width, T of the charge signal, and the time when the driving voltage is applied to the transducer is controlled by the strobe signal.

The driver circuit 300 draws power from the power supply only when the pulsed voltage VT is present. Further, minimal energy is drawn when the charge pulse is not present. Most of the energy drawn from the power supply is provided to the transducer. This minimizes power consumption and provides for high efficiency, important factors where the monitor is powered exclusively by internal batteries.

The driver circuit may be considered as having a charging part and a discharging part. The charging part includes a 12 millihenry inductor 303, a 200 volt ZVNL120A MOSFET switching transistor 304, manufactured by ZeTex Corporation, two type 1N4148 diodes connected in series and shown as a single diode 305, a 0.001 microfarad, 200 volt capacitor 306, and a 200 ohm resistor 307. The inductor 303 and the transistor 304 are connected at a node 310, and are further connected between the positive power supply terminal T+ and the circuit ground 308. Node 310 is also connected to the anode of the diode 305. The cathode of the diode 305 is connected to the circuit ground 308 through the series circuit of a node 311, the capacitor 306, a node 312, and the resistor 307.

To maximize energy conservation, the pulsed voltage VT is applied only when necessary. In the preferred embodiment, the pulsed voltage VT has a duration of about 3.7 milliseconds, which is sufficient to allow for charging the inductor 303, for charging the capacitor 306, for discharging the capacitor 306 through the transducer, and for any return signal to detected by the transducer. The charge signal on line 301 and the strobe signal on line 302 are applied during the interval when the pulsed voltage VT is being applied. When a charge pulse is applied to the gate of the transistor 304, the transistor is turned on and the power supply voltage VT forces a current 309 through the inductor 303 and the transistor 304 to the circuit ground 308. While the charge pulse is being applied the current 309 through the inductor 303 and the energy stored in the inductor 303 will both increase ($I = \int (V/L)\,dt$, $E = LI^2/2$). The duration of the charge pulse is preferably not so long as to cause saturation of the inductor 303. Preferably, the duration T of the charge pulse is sufficiently short that I is approximately a linear function of the duration T. A longer duration may be used but, in this case, the resistance of the inductor 303, the on-state resistance of the transistor 304, and the resistance of the power supply providing the pulsed voltage VT will have an effect and the current flow will be an exponential function. Therefore, if a longer duration is used it is preferable that the software account for the non-linearity. Thus, the magnitude of the current and the amount of energy stored in the inductor 303 are determined primarily by the duration T of the charge pulse.

When the charge pulse ends the transistor 304 is turned off, thereby interrupting the current flow. As is well known, when the current flow through an inductor is changed or interrupted the inductor will generate an output voltage which resists that change in the current flow, and the output voltage will be proportional to the degree of change or interruption (V=L di/dt). Therefore, when the transistor 304 is turned off the inductor 303 will generate a voltage which forces current into the capacitor 306 via the diode 305 and the resistor 307. The current forced into the capacitor 306 charges the capacitor and therefore generates a voltage (V=∫(I/C) dt) across the capacitor. The diode 305 acts as a peak detector and allows the inductor 303 to force current into the capacitor 306, thereby charging the capacitor, but prevents the capacitor 306 from discharging back through the inductor 303, or the transistor 304. The capacitor 306 has thereby been charged and the voltage across the capacitor 306 is thus proportional to the current through the inductor 303, and thus to the duration T of the charge pulse.

Another 1N4148 diode 313 is connected between node 312 and an output node 314. A 150 ohm resistor 315 is connected between the node 314 and the circuit ground 308. A first transducer terminal connection T1 is connected to the node 314, and a second transducer terminal connection T2 is connected to the circuit ground 308. The transducer is connected across terminals T1 and T2. When the inductor 303 is forcing current into the capacitor 306 to charge the capacitor, this current will develop a voltage across the resistor 307. The diode 313 prevents this voltage from being applied to the transducer, thereby preventing the transducer from generating an undesired pulse.

The discharging part of the driver circuit 300 primarily includes another ZVNL120A transistor 316, the capacitor 306, and the diode 313. The transistor 316 is connected between the node 311 and the circuit ground 308. When a strobe pulse is applied to the gate of the transistor 316, the transistor is turned on and the capacitor 306 provides an output voltage VD across terminals T1 and T2 and discharges through the diode 313 and the transducer. The capacitor 306 also discharges through resistors 307 and 315. In the preferred embodiment, the output voltage VD ranges from 20 to 160 volts. Also, in the preferred embodiment, the strobe signal is applied immediately after the charge signal is terminated. This prevents the capacitor 306 from self-discharging and maximizes the efficiency of the circuit.

The value selected for the resistor 307 is a compromise between two conflicting goals: the value should be as low as possible, so as to efficiently charge the capacitor 306; and should be as high as possible, so that the capacitor 306 will discharge primarily through the transducer and not through the resistor 307. The transducer both emits a pulse and detects any return signal. The resistor 315 and the resistor 307 act as a load or damping resistor for the transducer when any return signal is present. The value selected for the resistor 315 is a compromise between two conflicting goals: the value should be as high as possible so that the energy stored in the capacitor 306 is efficiently provided to the transducer; and should be low enough to provide, in conjunction with the resistor 307, a proper load for the transducer.

In the operation of the preferred embodiment, the software determines the voltage that is to be applied to the transducer and, thus, the required duration T of the charging pulse. The charging pulse is then applied for the duration T, which causes energy to be stored in the inductor 303. When the charging pulse is terminated this causes a high voltage to be developed across the capacitor 306. Then, when the transducer operation is desired, the software applies the strobe pulse, which causes the capacitor 306 to apply a high voltage pulse VD to the transducer. Therefore, the voltage VD applied to the transducer is readily determined and controlled by the duration T of the charging pulse. This circuit provides for high efficiency and is thus advantageous over conventional circuits which use a transformer to generate the high voltage for driving the transducer.

Figure 20:
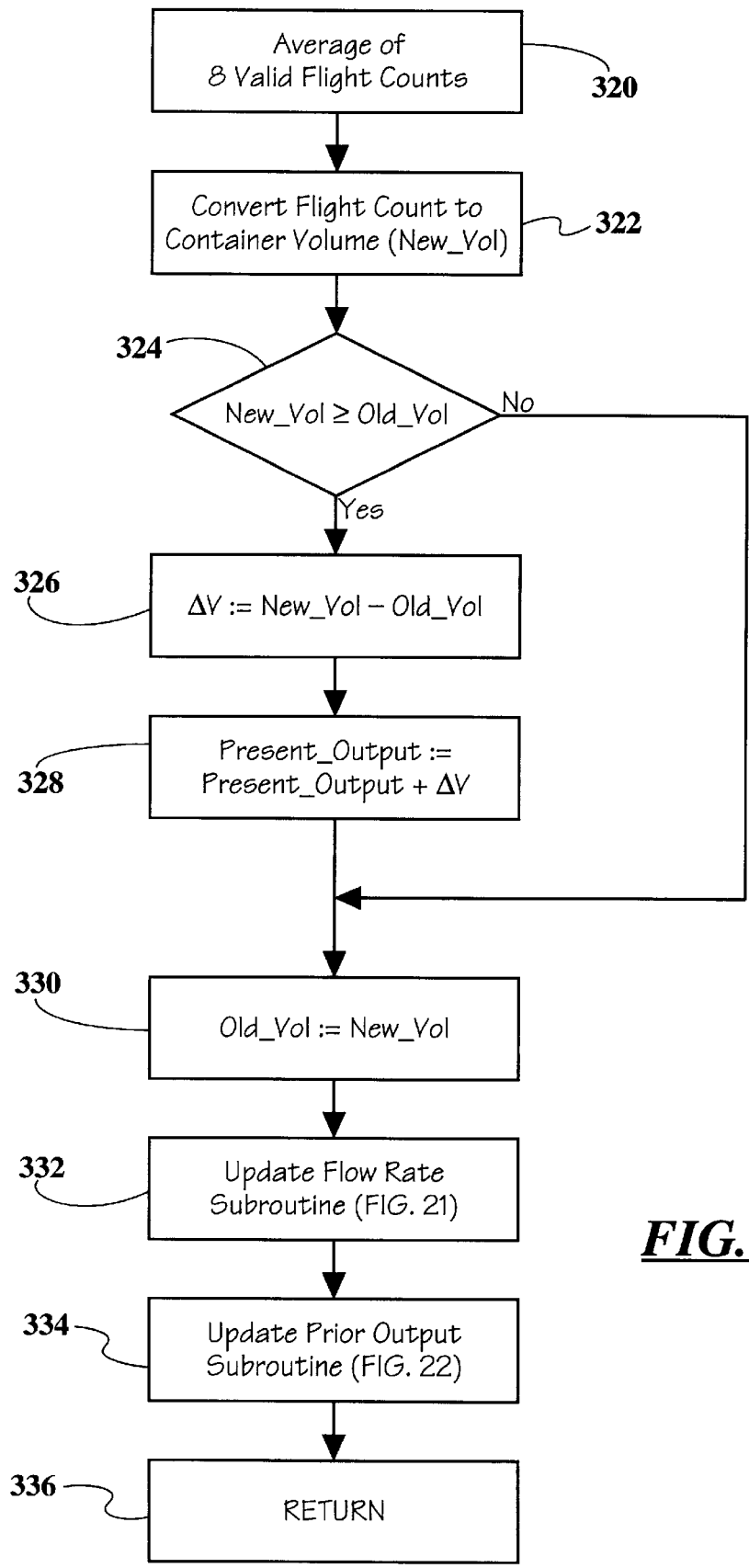
FIG. 20 is a flow chart showing the operation of the software which controls the fluid output monitor of FIG. 1.

The operation of the software which controls the monitor 10 will now be explained with reference to FIGS. 20–22. Referring first to FIG. 20, the software at 320 takes the average of a predetermined number of flight counts as passed to it by the transducer driving routine (see discussion of FIG. 18, above). In the disclosed embodiment the software takes the average of the most recent eight valid flight counts. This average of the last eight valid flight counts is then converted to a container volume at 322 by using a look-up table, a mathematical algorithm, or a combination of the two. The container volume is then assigned to a variable New_Vol. At 324 the new container volume is compared to the previously determined container volume, as stored in the variable Old_Vol. If the new container volume is greater than or equal to the previously determined container volume, indicating that the container 14 is not being emptied, then the change in volume since the previously determined container volume is calculated at 326 and assigned to the variable ΔV. The fluid output for the present time interval, as stored in the variable Present_Output, is then incremented at 328 by the change in volume ΔV.

At 330 the previously determined container volume Old_Vol is assigned the value of the new container volume New_Vol. A subroutine for updating the flow rate is run at 332, a routine for updating the prior output is run at 334, and control is passed at 336 back to the top of the loop at 320.

If it is determined at 324 that the container 14 is being drained, that is, the new container volume is less than the previously determined container volume, then steps 326 and 328 are bypassed, and the previously determined container volume is reassigned the value of the new container volume at 330.

Figure 21:
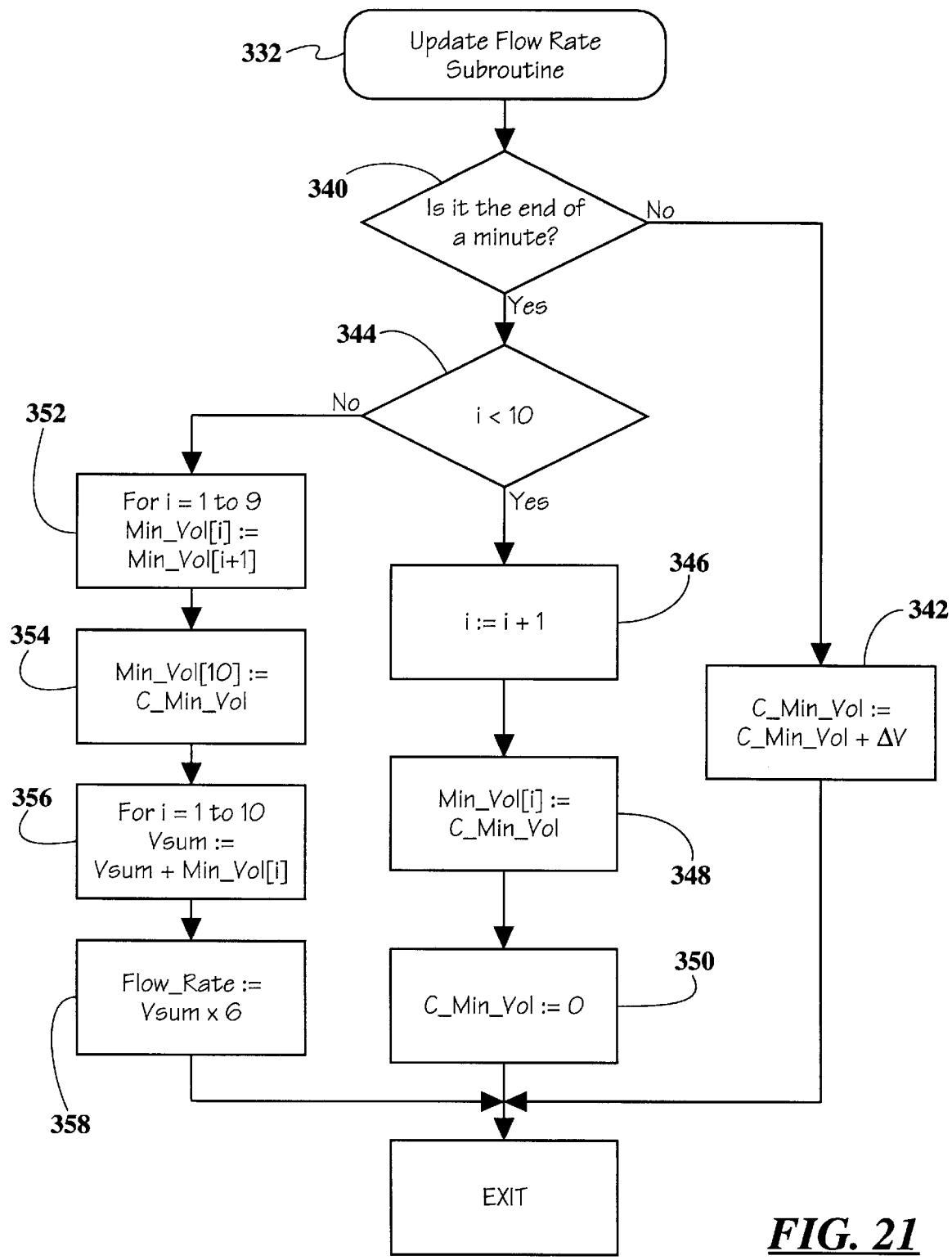
FIG. 21 is a flow chart of a first subroutine of the software which is the subject of the flow chart of FIG. 20.

FIG. 21 illustrates the subroutine 332 for updating the flow rate. At 340 the subroutine checks the system clock to determine whether it is the end of a minute. If not, then the current minute volume, represented by the variable C_Min_Vol, is incremented at 342 by the change in volume ΔV as calculated at 326 of the main control routine (FIG. 20). The subroutine then terminates.

However, if it is determined at 340 that it is the end of a minute, then the flow rate is updated. First, the subroutine checks at 344 to determine whether ten minutes worth of patient flow information has been accumulated, since the flow rate is based on the last ten minutes' data. To accumulate this information, an array is created, and each of the first ten minutes' patient flow rate is placed in the array. If it is determined at 344 that less than ten minutes worth of patient data has been compiled, that is, the current minute, represented by the variable i, is less than 10, then the array continues to fill. The current minute is incremented by 1 at 346. At 348 the volume for the selected minute, represented by the variable Min_Vol[i], is assigned the value of the current minutes' volume C_Min_Vol. The current minutes' volume C_Min_Vol is then reset to 0 at 350. The subroutine then terminates.

If it is determined at 344 that ten minutes worth of patient flow data has been accumulated, that is, the value of the variable i is not less than 9, then the array is full, and it becomes necessary for stored values to be moved down the array, in effect bumping the oldest value from the array. This is accomplished at 352 by a loop in which, for i=1 to 9, each value Min_Vol[i] is assigned the value of the succeeding minute's volume Min_Vol[i+1]. The volume for the tenth minute, Min_Vol[10], is then assigned the value of the current minute's volume C_Min_Vol at 354.

The total output for the preceding ten-minute period is calculated at 356 as follows. Once the array has been updated, then a loop is executed in which a variable Vsum is assigned the previous value of Vsum plus the output volume for the next one-minute interval. This loop is repeated ten times, once for each of the stored minutes.

Once the total output for the preceding ten-minute period is calculated, the output at 358 is multiplied by six (the number of ten-minute periods in an hour) to yield an output in terms of milliliters per hour. This flow rate is then displayed in the flow rate display 218.

Figure 22:
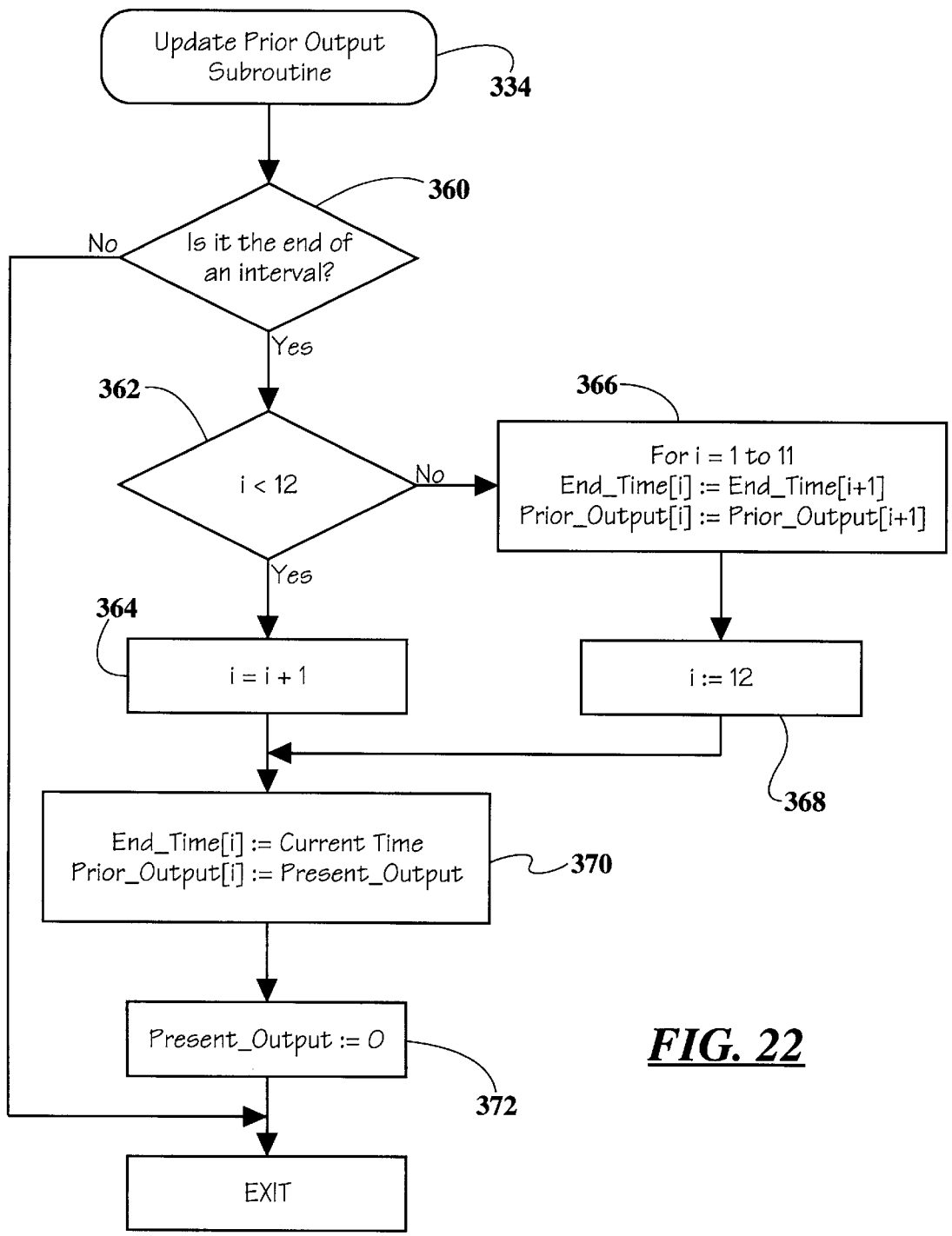
FIG. 22 is a flow chart of a second subroutine of the software which is the subject of the flow chart of FIG. 20.

FIG. 22 shows a flow chart for the subroutine 334 which updates the prior output. At 360 the system clock is checked to determine whether it is the end of an interval. It will be recalled that the length of the interval is user-definable and can be a period of either five, ten, fifteen, twenty, or thirty minutes or one or two hours. If it is not the end of an interval, the subroutine 334 terminates. If it is the end of an interval, then the subroutine checks at 362 to determine whether the variable i is less than 12. As previously explained, the monitor 10 of the disclosed embodiment can store output fluid data for up to twelve prior intervals. If the number of prior intervals for which fluid output data is stored is less than 12, then data for the interval is simply assigned to the next prior interval at 364 by incrementing the variable i by one, and the fluid output data for that interval is stored in an array. However, if twelve prior intervals are already stored, then each value in the array is bumped down, knocking the oldest prior interval off the array. This updating of the array is achieved at 366 by a loop in which, for i=1 to 11, the end time of the interval is set to the end time of the next interval, and the output for that interval is set to the output for the next interval. The variable i is then set to 12 for the most recent prior interval, as shown in block 368.

At 370 the subroutine next sets the end time for the most recent prior interval to the current time, and the output for the most recent prior interval is set to the present interval output. The present interval output is then reset to zero at 372, and the subroutine terminates.

It will be understood that the flow charts of FIGS. 20–22 are simplified flow charts intended to illustrate general principles of operation of the operating software for the urine monitor 10 and that nonessential details of the software have been omitted for purposes of clarity.

Operation of the urine monitor 10 to track urine output from a catheterized patient will now be explained. The patient is first catheterized, using a conventional Foley catheter 132. The monitor 10 is then hung on the patient bedframe, ensuring that the unit hangs freely, or the monitor 10 is set on the floor in a safe location. The monitor 10 is then powered up by pressing the on/off button 200 on the control panel 18. The lid 16 of the housing 12 is raised, and a disposable container 14 is positioned within the cavity 42 defined within the housing. The base 112 of the container 14 is positioned behind the upstanding stop members 46 on the angled lower walls 44 of the housing 12. The upper end of the container 14 is pivoted rearward until the rear panel 101 of the container confronts the back panel 36 of the housing 12. The lid 16 is then closed. As the lid 16 descends, the collar 24 formed on a lower surface 26 of the lid will engage the vented cap 30 mounted atop the container 14. The rounded upper surface of the lid 30 will cause the lid to center itself within the collar 24, centering the container 14 in an upright position and retaining the upper end of the container within the cavity 42 of the housing. Latching the lid 16 by means of its associated magnetic latches exerts a slight downward force on the container 14, urging it into snug engagement with the base of the cavity 42.

With the container 14 thus mounted within the cavity 42 of the housing 12, the outlet port 114 at the lower end of the container resides within the channel 48 in the lower portion 40 of the housing 12. The portion of the base 112 rearward of the outlet port 114 rests on the floor 50 formed at the base of the cavity 42. The ultrasound transducer 52 mounted on the horizontal floor 50 adjacent the rearward terminus of the channel 48 snugly engages the flat base 112 of the container 14 and is acoustically coupled thereto.

With the lid 16 thus closed, the inlet port 35 at the upper end of the container 14 extends upward through the cutout section 34 formed along the left edge of the lid. The rearward end of the Foley catheter tube 132 is coupled to the inlet tube 35, and the plug at the rearward end of the temperature sensor of the Foley catheter is plugged into the corresponding jack on the edge of the lid 16.

When the urine monitor 10 is powered up, the optical sensor 32 located within the collar 24 on the lower surface 26 of the lid 16 projects a beam of light downward and at an angle. Under normal circumstances the light beam will reflect off the central portion 144 of the cap 30 atop the disposable container 14 and reflect upward. If the optical sensor 32 detects a reflected beam, operation of the urine monitor 10 will proceed normally. However, in the event that the optical sensor 32 fails to detect a reflection, indicating that a container 14 is not positioned within the cavity 42 of the housing 12, or perhaps that the lid 16 has not been completely closed, a "check container" message will be displayed in the user interface and alert message display 214. While the "check container" alert condition exists, all flight count data will be disregarded by the monitor, and the patient output flow data will not be updated. When the condition has been corrected and the optical sensor 32 detects a reflected beam, indicating that a container 14 is properly installed, normal operation of the urine monitor 10 will resume.

As urine from the catheterized patient enters the disposable container 14 via the inlet tube 35, the first three milliliters of urine will pool in the well 108 at the lower end of the container 14. Because the well 108 has a relatively narrow cross-sectional area, the depth of the pool will increase rapidly as the well fills. Since the transducer of the disclosed embodiment can obtain an accurate reading of a column of fluid having a height of as little as about one millimeter, an accurate volumetric measurement can be obtained with as little as about 2 milliliters of urine in the well 108 of the container 14.

As urine continues to collect in the container 14, the ultrasound transducer circuitry continues to measure flight counts to determine a container volume. The software employing the algorithm outlined in FIG. 20 computes a new present interval output volume. That volume is displayed in the present interval output display 204 and is continuously updated. In addition, the software multiplies the urine output for the preceding ten-minute period by six to calculate a flow rate in milliliters/hour, which is then displayed in the output flow rate display 218. If the calculated patient output flow rate exceeds or falls below predetermined parameters, the numbers in the display 218 indicating the flow rate will flash, optionally accompanied by an audible alarm. In addition, the appropriate alert message "high alarm" or "low alarm" is displayed in the user interface and alert message display 214 to apprise the medical personnel whether the alarm condition exists as a result of the flow rate being too high or too low.

In addition, the patient's bladder temperature, as detected by the thermistor temperature sensor in the forward end of the Foley catheter, is continuously displayed in the bladder temperature display 206. If for some reason a signal is not being input into the jack on the edge of the lid 16, either because the temperature sensor in the catheter has not been plugged in to the jack, or because of a failure of the thermistor temperature sensor, the alert message "check probe" will be displayed in the user interface and alert message display 214, optionally accompanied by an audible alarm. If the sensed bladder temperature exceeds or falls below predetermined parameters, the numbers in the display 206 which indicate the bladder temperature will flash, optionally accompanied by an audible alarm. In addition, the appropriate alert message "high alarm" or "low alarm" is displayed in the user interface and alert message display 214 to apprise the medical personnel whether the alarm condition exists as a result of the bladder temperature being too high or too low.

When the initial time interval has expired, the total urine output for that time interval is stored in memory. The total output for that time interval is also displayed in the display 216 which shows output for a prior time interval. The display 216 is also updated to show the time at which the prior interval ended. The present interval output display 204 is reset to zero, and the output for the present interval, now the second time interval, begins to accumulate. The bladder temperature display 206 is not affected by the changing of the time interval, nor is the calculated flow rate, which is calculated based upon a ten-minute moving window irrespective of whether that moving window bridges two time intervals. If at any time the operator wishes to obtain a reading of the entire fluid content of the container 14, the operator can press the container volume button 222. When the button 222 is pressed, the flow rate as displayed in the display 218 is replaced by a display indicating the volume of fluid in the container 14. Concurrently, the words "flow rate" in the display 218 are replaced by the words "container volume," and the designation "ml/hr" is replaced by the designation "ml." Thirty seconds after the container volume button 222 is released, the display 218 will revert to showing the calculated flow rate in milliliters/hour.

As can be seen, the control panel 18 continuously displays the urine output for the present time interval in the display 204 and continuously displays the total output for the preceding time interval in the display 216. If the operator wishes to access information concerning earlier time intervals, such information can be displayed by pressing the "up arrow" and "down arrow" keys 220, 221. Using FIG. 16 as an example, the length of the time interval is one hour, and the preceding time interval ended at 2:00 PM. If the operator presses the "down arrow" key 221 once, the display 216 will change to show the time interval which ended at 1:00 PM and would show the urine output for that time interval in the right-hand portion of the display 216. Simultaneously, the display 218 would change to show the cumulative output beginning with the time interval which ended at 1:00 PM up to and including the most recent prior time interval. The words "flow rate" in the display 218 would be replaced by the words "cumulative output," and the designation "ml/hr" would be replaced by the designation "ml." If the "down arrow" key 221 is pressed a second time, the display 216 would change to reflect the time interval ending at 12:00 PM and would show the urine output for that time interval in the right-hand portion of the display 216. Similarly, the display 218 would be updated to reflect the cumulative output beginning at the time interval which ended at 12:00 PM up to and including the most recent prior interval. The operator can thus use the "up arrow" and "down arrow" keys 220, 221 to access and to display stored information for preceding time intervals. In the disclosed embodiment the monitor 10 stores the previous twelve interval output values.

If, during the operation of the urine monitor 10, the monitor becomes tilted from a vertical position, then one of two things will happen, depending upon the severity of the tilt. First, if the monitor is tilted at less than about 4°–6° from vertical, the immediate effect would be that the surface of the liquid within the container 14 would no longer be perpendicular to the axis of propagation of the sound waves emitted by the transducer 52. Consequently the reflection at the liquid/air interface will return at an angle to the axis of propagation, resulting in a weak or undetectable return signal. The transducer driving routine, detecting a weak signal, would boost the output signal for the next cycle, which will increase the likelihood that the return signal will be detectable by the transducer 52 despite the tilting of the monitor.

Second, if the monitor 10 should become tilted from a vertical position by more than about 4°–6°, an angle sensor of conventional design located within the monitor will be activated. The alert message "not level" will be displayed in the user interface and alert message display 214.

The monitor 10 constantly examines the height of the column of urine in the container 14. If the height of the column reaches a predetermined value corresponding to 2,000 milliliters of urine, a "full container" alarm is triggered. The words "full container" will flash in the user interface and alert message display 214, optionally accompanied by an audible alarm. If the user presses the container volume button 222 while the "full container" condition exists, the flow rate as displayed in the display 218 is replaced by a display indicating the volume of fluid in the container 14, and the number indicating the volume of fluid in the container will flash.

In addition, the monitor 10 constantly examines the state of charge of the battery which powers the monitor. If the voltage of the battery falls below a predetermined level, indicating substantial discharge, the words "low battery" will flash in the user interface and alert message display 214.

In the event that an alarm condition arises and the audible alarm feature is active, the operator can silence the audible alarm by pressing the "alarm silence" key 224 on the control panel 18. When the "alarm silence" key 224 is pressed, the "alarm silenced" message is displayed in the user interface and alert message display 214 and will continue to be displayed until the alarm condition is corrected.

On certain occasions, such as when a patient is diuresing, urine output will exceed the capacity of the disposable container 14. On other occasions it may be necessary to withdraw a specimen from the container 14 for purposes of analysis. On these occasions it becomes necessary to discharge urine from the container 14. Discharging the contents of the container 14 is accomplished in the same manner as for a conventional urine collection bag, that is, the clip 128 at the free end of the rubber tubing 126 is disengaged from the "doghouse" 124 on the front panel 100 of the container 14. The tubing 126 is extended downward through the channel 48, and the spring clamp 129 on the tubing 126 is released, permitting the contents of the container 14 to be discharged. When the desired amount of urine has been discharged from the container 14, the spring clamp 129 is re-engaged, the tubing is bent upward, and the clip 128 at the free end of the tubing 126 is again engaged with the doghouse 124 on the front panel 100 of the container 14.

When the contents of the container 14 are being discharged, the operating software of the monitor 10 will perceive that the flight count is diminishing, rather than increasing as would normally be the case (see box 324, FIG. 20). The monitor 10 stores a value in memory corresponding to the container volume, and waits until the flight count once again begins increasing, signaling the end of the discharge sequence. The monitor thereafter adjusts all future readings to compensate for the volume of urine discharged from the container.

The monitor 10 can be powered down by the operator pressing the on/off button 200 on the control panel 18. To prevent the inadvertent loss of information arising from accidental actuation of the on/off button 200, measurement data continues to be stored for ten minutes after the unit is powered off. If the operator desires to clear patient data without powering off the unit, he can do so by pressing the "patient data reset switch" 202 on the control panel 18 and holding the switch for two seconds. To prevent inadvertent loss of patient data by accidental actuation of the "patient data reset switch" 202, the switch must be depressed for two full seconds to activate. A short audible "beep" will sound after the "patient data reset switch" 202 has been depressed for two full seconds, signaling that the reset has been completed.

A unique feature of the urine monitor 10 of the disclosed embodiment is the provision for time intervals of user-definable length. In critical care environments, it is often preferred to monitor a patient's urine output over longer time intervals, for example, one or even two hours. In contrast, in operating room environments where more up-to-the-minute information is vital, shorter time intervals such as fifteen or twenty minutes may be more desirable. Prior art electronic urine monitors have provided time intervals of fixed duration, resulting in a monitor which may be well suited for critical care environments but not operating room environments, or which may be well suited for operating room environments at the expense of critical care environments, or which may represent a compromise which is not optimally suited for either environment. By providing for time intervals of user-definable duration, a single monitor can be easily adapted for movement between critical care and operating room environments and can be quickly and easily adjusted for optimum performance in either environment.

Another feature of the urine monitor 10 of the disclosed embodiment is the provision of a disposable container 14 having a vertical inlet tube 35 and a vertical outlet tube 114. The vertical inlet tube 35 provides the advantage that the catheter tubing 132 is less likely to bend below the level of the inlet port when the tubing is draped from the patient to the monitor 10, which bending would cause a loop where fluid would pool. The pooled fluid would not enter the container 14 and would thus not be registered as output unless the tubing 132 was physically manipulated by the clinician. When the tubing 132 is manipulated, all of the pooled fluid enters the container at once, causing a sudden increase in the volume of fluid within the container 14 and possibly skewing the measurements.

As for the outlet tube 114, its vertical orientation permits significant improvements in drainage over prior art containers. In prior art urine containers for electronic urine monitors, to keep the bottom surface of the container free of obstructions which might hinder coupling of the transducer to the container, the outlet tube was located on the front of the container. Such an arrangement requires that the monitor be tilted to drain the container completely. In contrast, by placement of the outlet tube 114 on the base 112 of the container, the outlet tube can be oriented vertically, and the container can be completely drained without having to tilt or manipulate the monitor 10.

Another feature of the disclosed embodiment 10 is the provision of a well 108 at the lower end of the container 14. Sound waves will reflect off of any interface between substances of different transmissivity. Thus some of the sound wave energy will tend to reflect off of the interface between the base 112 of the container 14 and the fluid covering the base. The reflection which the transducer circuitry attempts to measure is the reflection off of the interface between the upper surface of the liquid in the container and the air above it. Because of limitations inherent in transducer design, when the interface at the upper surface of the liquid pool is too close to the interface at the base of the container, the transducer is unable to differentiate the two reflections. Thus there is a minimum distance by which the liquid/air interface must be separated from the base of the container in order for the transducer to obtain an accurate reading.

In prior art containers at least five milliliters of liquid must be present in the container before the liquid/air interface is distinguishable by the transducer. Even when five milliliters of liquid are present in the prior art containers, however, the measurement is often inaccurate. Surface tension can cause the container to fill unevenly. Further, the consequences of tilting of the container are magnified at smaller volumes.

The container 14 of the present invention overcomes these problems by providing the well 108 at the base 112 of the container. The well 108 has a significantly smaller cross-sectional area than the remaining portion of the container 14. The well greatly enhances the sensitivity of the transducer to even small amounts of liquid and ensures that small volumes of liquid are concentrated directly above the transducer. Consequently, even a small amount of fluid—less than two milliliters—can provide a depth sufficient for the transducer to obtain an accurate reading. Further, effects of tilting and of surface tension are reduced.

Another feature of the urine monitor 10 concerns the filter vent cap 30 which fits atop the disposable container 14 and performs several functions. First, it houses and protects the filter element 139. The pattern of protective ribs 140, 142 permits ventilation while protecting the filter against objects such as pens, fingers, or the like damaging or dislodging the filter. Second, the dome-shaped upper surface provides a contact area which engages the cooperating mating surface on the lower surface of the lid 16 of the housing 12 to assure adequate downward pressure to seat the lower end of the container against an ultrasound transducer 52. The dome-shaped cap 30 is forgiving in the event of a slight mismatch with the mating surface on the cover. Third, the flat upper surface 144 of the cap 30 reflects the projected light beam of the optical sensor 32 to verify to the electronic module that a container is in place in the housing.

While all of these features are advantageously provided by the cap 30 in the disclosed embodiment, it will be appreciated that some of these features can be provided by other structures. For example, the optical sensor 32 could be repositioned to direct its light beam at another portion of the container 14 to determine whether the container is in place. An appropriate reflective surface could be provided at the corresponding location on the container 14 by means such as a circle of reflective tape adhered to the container.

According to conventional nursing procedures, an attending clinician will typically need to record a "shift total" of the patient's urine output, i. e., the volume of urine discharged by the patient during the clinician's nursing shift. According to prior art fluid output monitors, within certain restrictions a nurse could quickly ascertain the "shift total" by pressing the container volume key, the resulting displayed value corresponding to the shift total. However, for this procedure to work, it was necessary for the nurse to empty the container at the beginning of the nurse's shift. Further, if it became necessary for the container to be emptied mid-shift, then the container volume at the end of the nurse's shift would not correspond to the shift total.

In addition, conventional nursing procedures also call for the attending clinician to record urine output on an hourly basis. The prior art fluid output monitor disclosed in the aforementioned U.S. Pat. No. 4,448,207 and U.S. Pat. No. 4,658,834 would store only the most recent prior output interval value in addition to the present interval output. Once the next time interval had passed, the preceding prior output interval value was discarded. Thus the nurse had to inspect the monitor every hour to chart the fluid output value for the preceding hour. If the nurse was unable to inspect the monitor during a particular hour, the fluid output value for the preceding hour would be lost.

The fluid output monitor 10 of the disclosed embodiment addresses both of these problems. Because the monitor 10 records fluid output data for up to twelve preceding time intervals, the nurse can wait until the end of the shift and then use the up- and down-arrow keys 220, 221 to step back through each hour of his or her shift, recording the fluid output for each interval. Thus there is no need for the nurse to review the monitor each hour or risk losing patient output fluid data. Further, when the nurse has stepped back to the first prior time interval of his or her shift, the cumulative output shown in the display 218 will correspond to the "shift total." This will be the case whether or not the container 14 was emptied at the beginning of the shift, and whether or not the container was emptied mid-shift.

Finally, it will be understood that the preferred embodiment has been disclosed by way of example, and that other modifications may occur to those skilled in the art without departing from the scope and spirit of the appended claims.

What is claimed is:

1. An apparatus for measuring a liquid discharged from a patient's body, comprising:

a housing defining a cavity, said cavity having a floor;

a substantially rigid wall container removably positioned within said cavity, said container having a bottom wall portion supported on said floor of said cavity;

means for introducing said discharged liquid into the interior of said container to form a pool on an interior surface of said bottom wall portion;

a transducer mounted in said floor and engaging said bottom wall portion of said container;

means for periodically engaging said transducer to transmit energy through said bottom wall portion and said pool;

means for determining the time duration required for said transmitted energy to travel from said transducer means to the upper surface of said pool and back again;

light sensor means mounted on said housing adjacent said cavity for projecting a beam of light and for receiving a reflected beam of light;

a reflective surface on said container disposed when said container is positioned within said cavity so as to reflect said projected light beam back toward said light sensor means; and means for detecting whether said light sensor is receiving said reflected beam of light and for providing an indication if said reflected beam is not detected;

whereby said light sensor receives said reflected beam of light only when a container is positioned within said cavity.

2. The apparatus of claim 1, wherein said container further comprises an opening and a cap covering said opening, and wherein said reflective surface comprises a surface of said cap.

3. The apparatus of claim 1, wherein said housing further comprises a lid pivotably mounted adjacent its upper end, wherein said light sensor is mounted on said lid, and wherein said light sensor receives said reflected beam of light only when said lid is properly closed and a container is positioned within said cavity.

4. An apparatus for measuring a liquid discharged from a patient's body, comprising:

a housing defining a cavity having a floor;

a substantially rigid wall container removably positioned within said cavity, said container having a bottom wall portion supported on said floor of said cavity;

means for introducing said discharged liquid into the interior of said container to form a pool on an interior surface of said bottom wall portion;

a transducer mounted in said floor and engaging said bottom wall portion of said container;

means for periodically engaging said transducer to transmit energy through said bottom wall portion and said pool;

means for determining the time duration required for said transmitted energy to travel from said transducer means to the upper surface of said pool and back again;

a channel formed in said floor of said cavity; and an outlet tube projecting downward from said bottom wall portion of said container for discharging a liquid from the interior of said container, said outlet tube residing within said channel when said container is positioned within said cavity;

whereby said outlet tube being located on said bottom wall portion of said container permits said container to be completely discharged without having to tilt said container or said housing.

5. An apparatus for measuring a liquid discharged from a patient's body, comprising:

a housing defining a cavity having a floor;

a substantially rigid wall container removably positioned within said cavity, said container having a bottom wall portion supported on said floor of said cavity;

means for introducing said discharged liquid into the interior of said container to form a pool on an interior surface of said bottom wall portion;

a transducer mounted in said floor and engaging said bottom wall portion of said container;

transducer driving means for periodically engaging said transducer to transmit energy through said bottom wall portion and said pool;

flight count means for determining the time duration required for said transmitted energy to travel from said transducer means to the upper surface of said pool and back again;

means responsive to said flight count means for determining the volume of fluid introduced into said container during a predetermined period of time, the duration of said predetermined period of time being adjustable by a user.

6. An apparatus for measuring a liquid discharged from a patient's body, comprising:

a housing defining a cavity having a floor;

a substantially rigid wall container removably positioned within said cavity, said container having a bottom wall portion supported on said floor of said cavity;

means for introducing said discharged liquid into the interior of said container to form a pool on an interior surface of said bottom wall portion;

a transducer mounted in said floor and engaging said bottom wall portion of said container;

means for periodically engaging said transducer to transmit energy through said bottom wall portion and said pool;

means for determining the time duration required for said transmitted energy to travel from said transducer means to the upper surface of said pool and back again; and a well formed in a lower portion of said container, said well having substantially vertical side walls and a relatively small cross-sectional area, said well being disposed directly above said transducer when said container is positioned within said housing, said container being configured to direct an initial amount of liquid introduced into said container into said well, whereby small volumes of liquid in said container are concentrated in said well directly above the transducer to permit measurement of small amounts of liquid in said container.

7. An apparatus for measuring a liquid discharged from a patient's body, comprising:

a housing defining a cavity having a floor;

a substantially rigid wall container removably positioned within said cavity, said container having a bottom wall portion supported on said floor of said cavity;

means for introducing said discharged liquid into the interior of said container to form a pool on an interior surface of said bottom wall portion;

a transducer mounted in said floor and engaging said bottom wall portion of said container;

transducer driving means for periodically engaging said transducer to transmit a pulse of energy through said bottom wall portion and said pool, said transducer driving means including means for driving said transducer at more than one level of output energy, and said transducer driving means further comprising means responsive to said transducer receiving a weak return signal for increasing the output energy level of a succeeding pulse of energy; and means for determining the time duration required for said transmitted energy to travel from said transducer means to the upper surface of said pool and back again.

* * * * *